United States Patent [19]
Kaji

[11] Patent Number: 5,262,090
[45] Date of Patent: Nov. 16, 1993

[54] 16-BENZALANDROSTA-1,4-DIENE-3,17-DIONE COMPOUNDS AND NON-LINEAR OPTICAL MATERIAL

[75] Inventor: Makoto Kaji, Hitachi, Japan

[73] Assignee: Hitachi Chemical Company, Ltd., Tokyo, Japan

[21] Appl. No.: 845,943

[22] Filed: Mar. 4, 1992

[30] Foreign Application Priority Data

Aug. 30, 1991 [JP] Japan ............... 3-219115

[51] Int. Cl.$^5$ ............... F21V 9/00; F21V 9/04; G02B 9/00; C07J 1/00
[52] U.S. Cl. ............... 252/582; 252/587; 252/589; 359/328; 552/528
[58] Field of Search ............... 552/528; 252/582, 587, 252/589; 359/328, 329

[56] References Cited

U.S. PATENT DOCUMENTS

| | | | |
|---|---|---|---|
| 3,007,946 | 11/1961 | Tyner | 552/528 |
| 3,163,641 | 12/1964 | Christiansen et al. | 552/528 |
| 4,416,821 | 11/1983 | van Rheenen et al. | 552/528 |
| 4,526,720 | 7/1985 | van Rheenen et al. | 552/528 |

Primary Examiner—Philip Tucker
Attorney, Agent, or Firm—Antonelli, Terry, Stout & Kraus

[57] ABSTRACT

Non-linear optical materials using a 16-benzalandrosta-1,4-diene-3,17-dione compound represented by the formula [I]

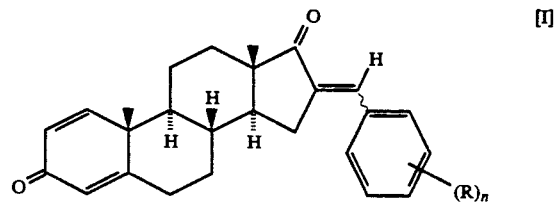

wherein R is hydrogen, alkyl or other specified substituents, have a high non-linear optical constant, and can provide a non-linear optical device having excellent properties.

50 Claims, 30 Drawing Sheets

16-BENZALANDROSTA-1,4-DIENE-3,17-DIONE COMPOUNDS AND NON-LINEAR OPTICAL MATERIAL

BACKGROUND OF THE INVENTION

The present invention relates to 16-benzalandrosta-1,4-diene-3,17-dione compounds which can be used in components for optical higher harmonic wave generation, electro-optical switching, and the like, a process for producing the compounds, and non-linear optical materials and non-linear optical components which use the same.

Non-linear optical materials, which are expected to play an important role in optical communication technology, exhibit such functions as optical mixing, parametric oscillation, optical higher harmonic wave generation and the like based on the non-linear optical susceptibility of the materials. Previously, inorganic crystals of $KH_2PO_4$, $NH_4H_2PO_4$ or the like have been used as said materials. These materials, however, have been unsatisfactory for meeting the requirements of the above-mentioned applications because of their deliquescence, low non-linear susceptibility and low damage threshold value.

Furthermore, since the first order and second order electro-optical effects, which can be used for optical switching, respectively arise from essentially the same non-linear polarization as that which gives rise to the second order and third order non-linear optical effects, the same material might be used to obtain the two kinds of effects. However, inorganic materials have a drawback of a relatively longer response time.

Organic non-linear optical materials, which make use of the polarization of their π-electron system, have a higher non-linear optical coefficient, no deliquescence in general and higher damage threshold value as compared with inorganic materials. Therefore, the research and development thereof is being actively forwarded in various fields. Recent results of such research and development are described in detail, for example, in Non-linear Optical Properties of Organic Molecules and Crystals, Vols. 1 and 2, edited by D. S. Chemla and J. Zyss (published by Academic Press, 1978).

However, no material has ever been found which has a sufficiently high non-linear optical coefficient to attain the intended purpose even in the case of low output lasers such as semiconductor lasers. Accordingly, further development of a novel non-linear optical material is eagerly awaited.

SUMMARY OF THE INVENTION

An object of the present invention is to provide a 16-benzalandrosta-1,4-diene-3,17-dione compound which can be used for a non-linear optical material with a high non-linear optical coefficient, a process for producing the same, and non-linear optical materials and non-linear optical component which use the same.

According to the present invention, there is provided a 16-benzalandrosta-1,4-diene-3,17-dione compound represented by the formula:

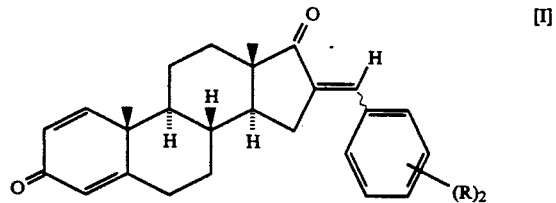

wherein R is a hydrogen, chlorine, bromine or fluorine atom, an alkyl group having 1–10 carbon atoms, an alkoxy group having 1–10 carbon atoms, an acetamido group having 1–10 carbon atoms, an aryl group having 6–10 carbon atoms, an alkylthio group having 1–10 carbon atoms, an aryloxy group having 6–10 carbon atoms, an arylthio group having 6–10 carbon atoms, an aralkyloxy group having 7–11 carbon atoms, or a mono- or dialkylamino group having 1–20 carbon atoms; n is an integer of 1 to 5, provided that when n is 2 or more, Rs may be the same or different from each other and the adjacent substituents may conjointly form a ring; and the bond shown by a wavy pattern indicates a cis- or trans-position.

Further, according to the present invention, there are provided a process for producing the compound of the formula [I], and non-linear optical materials and non-linear optical components which use the compounds of the formula [I].

DESCRIPTION OF THE PREFERRED EMBODIMENTS

Figure 1:
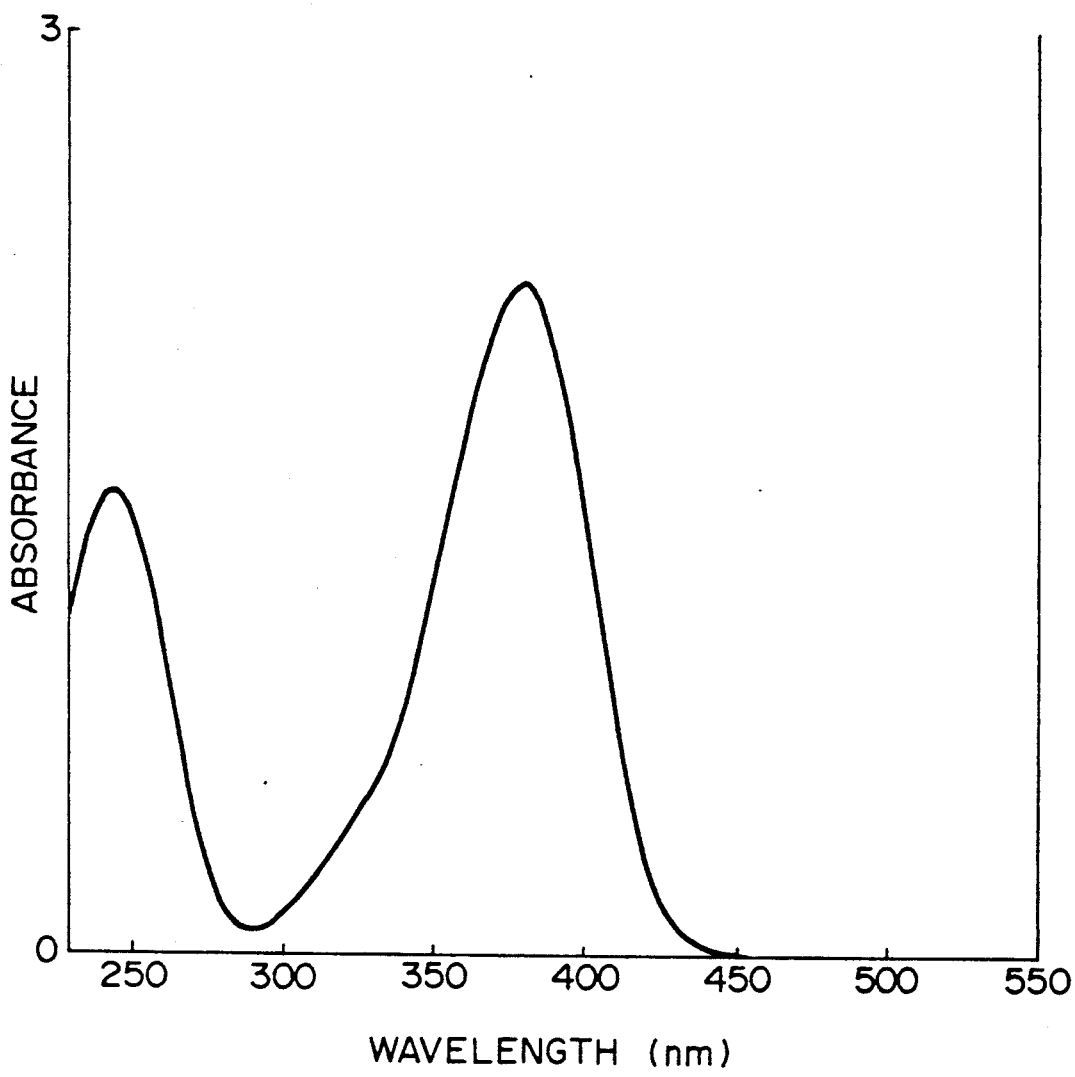
FIGS. 1 to 15 are ultraviolet-visible region absorption spectra of compounds of the formula [I] in methylene chloride solution.

The compounds of the present invention are represented by the formula:

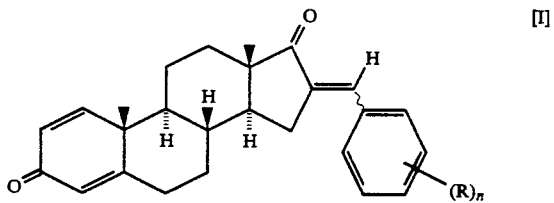

wherein R is a hydrogen, chlorine, bromine or fluorine atom, an alkyl group having 1–10 carbon atoms, an alkoxy group having 1–10 carbon atoms, an acetamido group having 1–10 carbon atoms, an aryl group having 6–10 carbon atoms, an alkylthio group having 1–10 carbon atoms, an aryloxy group having 6–10 carbon atoms, an arylthio group having 6–10 carbon atoms, an aralkyloxy group having 7–11 carbon atoms, or a mono- or dialkylamino group having 1–20 carbon atoms; n is an integer of 1 to 5, provided that when n is 2 or more, Rs may be the same or different from each other and the adjacent substituents may conjointly form a ring; and the bond shown by a wavy pattern indicates a cis- or trans-position.

Examples of the 16-benzalandrosta-1,4-diene-3,17-dione compounds represented by the formula [I] include the following:

16-(4'-methoxybenzal)androsta-1,4-diene-3,17-dione,
16-(4'-methylthiobenzal)androsta-1,4-diene-3,17-dione,
16-(4'-bromobenzal)androsta-1,4-diene-3,17-dione,
16-(4'-N,N-dimethylaminobenzal)androsta-1,4-diene-3,17-dione,
16(4'-N,N-dimethylamino-2,-fluorobenzal)-androsta-1,4-diene-3,17-dione,
16-(3',4',5'-trimethoxybenzal)androsta-1,4-diene-3,17-dione,
16-(2'-3'-dimethoxybenzal)androsta-1,4-diene-3,17-dione,
16-(4'-ethoxybenzal)androsta-1,4-diene-3,17-dione,
16-(4'-n-propoxybenzal)androsta-1,4-diene-3,17-dione,
16-(4'-n-butoxybenzal)androsta-1,4-diene-3,17-dione, 16-(4'-benzyloxybenzal)androsta-1,4-diene-3,17-dione,
16-(4'-chlorobenzal)androsta-1,4-diene-3,17-dione,
16-(3'-4'-methylenedioxybenzal)androsta-1,4-diene-3,17-dione,
16-(4'-acetamidobenzal)androsta-1,4-diene-3,17-dione,
16-(3'-methoxybenzal)androsta-1,4-diene-3,17-dione,
16-(2'-methylbenzal)androsta-1,4-diene-3,17-dione,
16-(3'-methylbenzal)androsta-1,4-diene-3,17-dione,
16-(4'-ethylbenzal)androsta-1,4-diene-3,17-dione,
16-(2',4'-dimethylbenzal)androsta-1,4-diene-3,17-dione,
16-(4'-fluorobenzal)androsta-1,4-diene-3,17-dione,
16-(2',4',5'-trimethoxybenzal)androsta-1,4-diene-3,17-dione,
16-(3',4'-dimethoxybenzal)androsta-1,4-diene-3,17-dione,
16-(2',4'-dimethoxybenzal)androsta-1,4-diene-3,17-dione,
16-(4'-phenoxybenzal)androsta-1,4-diene-3,17-dione,
16-(4'-phenylthiobenzal)androsta-1,4-diene-3,17-dione,
16-(4'-benzyloxybenzal)androsta-1,4-diene-3,17-dione, etc.

Preferred among them are the following compounds:
16-(4'-methoxybenzal)androsta-1,4-diene-3,17-dione,
16-(4'-methylthiobenzal)androsta-1,4-diene-3,17-dione,
16-(4'-bromobenzal)androsta-1,4-diene-3,17-dione,
16-(4'-N,N-dimethylaminobenzal)androsta-1,4-diene-3,17-dione,
16-(4'-N,N-dimethylamino-2,-fluorobenzal)-androsta-1,4-diene-3,17-dione,
16-(3',4',5'-trimethoxybenzal)androsta-1,4-diene-3,17-dione,
16-(2',3'-dimethoxybenzal)androsta-1,4-diene-3,17-dione,
16-(4'-ethoxybenzal)androsta-1,4-diene-3,17-dione,
16-(4'-n-propoxybenzal)androsta-1,4-diene-3,17-dione,
16-(4'-n-butoxybenzal)androsta-1,4-diene-3,17-dione,
16-(4'-benzyloxybenzal)androsta-1,4-diene-3,17-dione,
16-(4'-chlorobenzal)androsta-1,4-diene-3,17-dione,
16-(3',4'-methylenedioxybenzal)androsta-1,4-diene-3,17-dione, and
16-(4'-acetamidobenzal)androsta-1,4-diene-3,17-dione.

Further, the present invention relates to a process for producing said 16-benzalandrosta-1,4-diene-3,17-dione compounds which comprises reacting a substituted or unsubstituted aromatic aldehyde with androsta-1,4-diene-3,17-dione, non-linear optical materials comprising a composition containing said 16-benzalandrosta-1,4-diene-3,17-dione, and non-linear optical components which use said non-linear optical materials.

The 16-benzalandrosta-1,4-diene-3,17-dione compounds represented by the above formula [I] may be obtained by reacting a substituted or unsubstituted aromatic aldehyde with androsta-1,4-diene-3,17-dione by using the aldol condensation described collectively in, for example, Organic Reaction, Vol. 16.

As the substituted or unsubstituted aldehyde, there can be used benzaldehyde, 4-chlorobenzaldehyde, 4-bromobenzaldehyde, 4-fluorobenzaldehyde, 4-dimethylamino-2-fluorobenzaldehyde, 4-methoxybenzaldehyde, 4-methylthiobenzaldehyde, 4-aminobenzaldehyde, 4-methylaminobenzaldehyde, 4-dimethylaminobenzaldehyde, 4-ethylaminobenzaldehyde, 4-diethylaminobenzaldehyde, 4-dimethylamino-o-tolualdehyde, piperonal, vanillin, o-vanillin, p-tolualdehyde, 3,4-dimethoxybenzaldehyde, 2,3,4-trimethoxybenzaldehyde, 3,4,5-trimethoxybenzaldehyde, 3-chlorobenzaldehyde, 3-bromobenzaldehyde, 3-fluorobenzaldehyde, 3-methoxybenzaldehyde, 3-methylthiobenzaldehyde, 3-aminobenzaldehyde, 3-methylaminobenzaldehyde, 3-dimethylaminobenzaldehyde, 2-methoxybenzaldehyde, etc.

In the present invention, it is preferable to react 4-methoxybenzaldehyde, 4'-methylthiobenzaldehyde, 4'-bromobenzaldehyie, 4'-N,N-dimethylaminobenzaldehyde, 4'-N,N-dimethylamino-2'-fluorobenzaldehyde, 3',4',5'-trimethoxybenzaldehyde, 2',3'-dimethoxybenzaldehyde, 4'-ethoxybenzaldehyde, 4'-n-propoxybenzaldehyde, 4'-n-butoxybenzaldehyde, 4'-benzyloxybenzaldehyde, 4'-chlorobenzaldehyde, 3',4'-methylenedioxybenzaldehyde, 4'-acetamidobenzaldehyde or 4'-phenylbenzaldehyde with androsta-1,4-diene-3,17-dione.

The 16-benzalandrosta-1,4-diene-3,17-dione compounds according to the present invention can be obtained, for example, by condensing androsta-1,4-diene-3,17-dione with an equimolar or excessive molar amount of an aromatic aldehyde (the molar ratio of the steroidal compound to the aldehyde being preferable in the range of 1.0-1.8) in the presence of a catalyst and if necessary with heating, in a solvent of an amount between equal to and about 20 times the total weight of androsta-1,4-diene-3,17-dione and the aromatic aldehyde. Examples of preferred solvents are methanol, ethanol, 2-butanol, methyl Cellosolve, ethyl Cellosolve, tetrahydrofuran and dioxane. Examples of preferred catalysts are sodium hydroxide, potassium hydroxide, lithium hydroxide, barium hydroxide, tetramethylammonium hydroxide, piperidine, morpholine, sodium ethoxide, and sodium methoxide. These catalysts are used in an amount of 1-5% by weight relative to androsta-1,4-diene-3,17-dione. The reaction temperature is generally between room temperature and 150° C.

The non-linear optical material according to the present invention may comprise the 16-benzalandrosta-1,4-diene-3,17-dione compound represented by the above formula [I] used alone or may be a composition comprising said compound dispersed or dissolved in a macromolecular compound.

When the 16-benzalandrosta-1,4-diene-3,17-dione compound is used singly without mixing with other compounds, it can be used in the form of monocrystal, polycrystal, molecular glass or powder. In most cases it is used in the form of monocrystal because of its low optical loss and other reasons. The monocrystal of the 16-benzalandrosta-1,4-diene-3,17-dione compound can be grown from its solution by means of solvent evaporation or temperature reduction. The solvent used herein may be acetone, tetrahydrofuran, ethyl acetate, chloroform method such as the Bridgman's method or by the vapor phase growth method. It is also possible to obtain monocrystals or molecular glass which have a controlled direction of molecular orientation and an excellent non-linear optical property by heating and melting the 16-benzalandrosta-1,4-diene-3,17-dione compound represented by the formula [I] in the presence of a D.C. electric field and then cooling it gradually or rapidly while maintaining the electric field.

The macromolecular compounds used herein are, for example, homopolymers or copolymers of methyl acrylate, methyl methacrylate, ethyl acrylate, ethyl methacrylate, n-butyl acrylate, n-butyl methacrylate, cyclohexyl acrylate, cyclohexyl methacrylate, acrylic acid, methacrylic acid, styrene, vinyltoluene, divinylbenzene, vinyl chloride, β-hydroxyethyl acrylate, β-hydroxyethyl methacrylate, etc.; polyester, polyamide, polyurethane, polycarbonate, cellulose ester, polyether, and the like. The 16-benzalandrosta-1,4-diene-3,17-dione compound represented by the formula [I] and a corresponding monomer may be mixed and then polymerized by the action of heat or light to form an intended composition, or the macromolecular compound mentioned above and the 16-benzalandrosta-1,4-diene-3,17-dione compound represented by the formula [I] may be dissolved and mixed in a suitable solvent and then the solvent is removed to obtain a composition. The non-linear optical property of the composition can be improved by conducting poling during polymerization in the former case, or conducting poling after obtaining the composition both in the former case and in the latter case.

The non-linear optical material of the present invention can be used singly without mixing with other compounds in the form of bulk crystal, or as a part of waveguide type optical components including those of fiber type, slab type, plane type, and channel type. Non-linear optical components using the above-mentioned non-linear optical material include wavelength conversion components making use of second harmonic generation, sum frequency generation or optical parametric oscillation, and phase modulation components and polarization plane modulation components which make use of electro-optical effect.

The 16-benzalandrosta-1,4-diene-3,17-dione compound of the present invention has a high second order optical non-linearity since its molecule has a π-electron system of which the polarization increases further at the excited state. Furthermore, since it has an asymmetric steroid skeleton, its crystal inevitably assumes a structure devoid of centrosymmetry, so that it does not lose its second order optical non-linearity.

The present invention will be described in detail below with reference to Examples.

EXAMPLE 1

Figure 6:
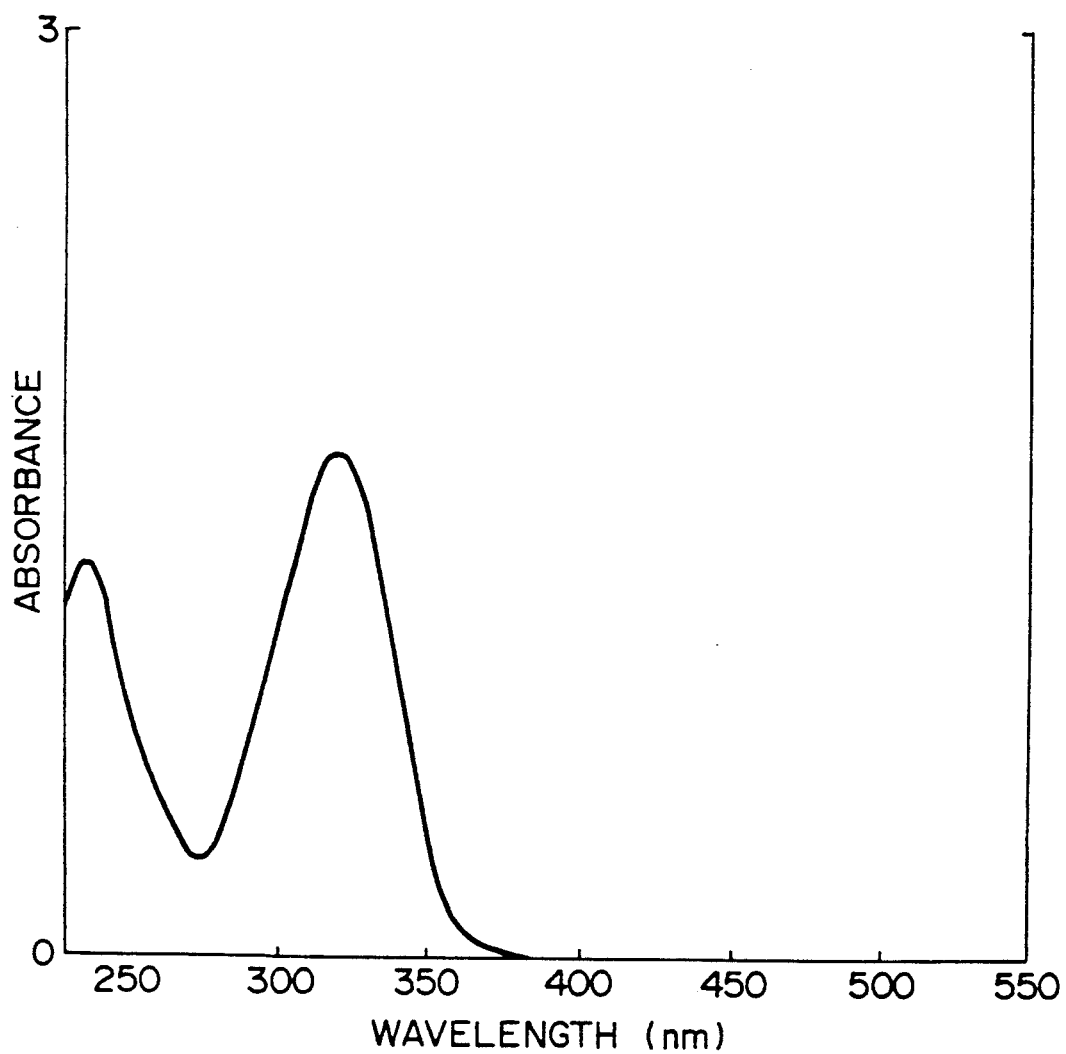

Synthesis of 16-(4′-N,N-dimethylaminobenzal)-androsta-1,4-diene-3,17-dione (compound 1) and second harmonic generation In a 50-ml pear-shaped flask were placed 1.5 g (5.28 mmols) of androsta-1,4-diene-3,17-dione and 788 mg (5.28 mmols) of 4-N,N-dimethylaminobenzaldehyde, then 3 ml of methanol and 0.5 ml of 40% aqueous sodium hydroxide solution were added thereto, a cooling tube was attached to the flask, and the mixture was heated under reflux for about 3 hours while being stirred with a magnetic stirrer. The reaction mixture was allowed to cool, and fine crystals thus precipitated were filtered with suction and washed thoroughly with methanol. The crystals were collected and dried overnight in a vacuum desiccator to give a yield of 1.4 g (64%). The ultraviolet-visible region absorption spectrum of the methylene chloride solution of the product is shown in FIG. 1 and the NMR spectrum of its $d_1$-chloroform solution is shown in FIG. 6. The structure of the compound was determined from the NMR spectrum and the ultraviolet-visible region absorption spectrum. The absorption maximum of the largest absorption band observed in the ultraviolet-visible region absorption, melting point, and second harmonic generation (abbreviated as SHG) efficiency determined by the powder method in the manner described below are shown in Table 1.

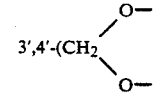

TABLE 1

| Compound No. | $(R)_n$ in the formula of Table 1 | $\lambda_{max}$[a] (nm) | M.p. (°C.) | SHG efficiency (urea ratio) |
|---|---|---|---|---|
| 1 | 4′-$(CH_3)_2$N— | 381.4 | 244.8 | 17.2 |
| 2 | 4′-$(CH_3)_2$N-2′- | 375.3 | 211.8 | 19.9 |
| 3 | 3′,4′,5′-$(CH_3O)_3$ | 321.8 | 163.2 | 10.9 |
| 4 | 2′,3′-$(CH_3O)_2$ | 296.6 | 203.1 | 7.2 |
| 5 | 4′-$CH_3O$— | 319.9 | 249.8 (decomposition) | 9.1 |
| 6 | 4′-$CH_3CH_2O$— | 321.8 | 195.7 | 5.6 |
| 7 | 4′-$CH_3CH_2CH_2O$ | 321.8 | 195.9 | 9.5 |
| 8 | 4′-$CH_3CH_2CH_2CH_2O$— | 322.5 | 204.3 | 6.7 |
| 9 | 4′-Phenyl-$CH_2O$— | 319.9 | 251.0 | 3.9 |
| 10 | 4′-$CH_3$S— | 337.8 | 267.5 | 17.3 |
| 11 | 4′-Cl | 299.1 | 263.8 | 4.8 |
| 12 | 4′-Br | 300.7 | 275 (decomposition) | 8.4 |
| 13 | 3′,4′-$(CH_2\langle{}^{O-}_{O-})$ | 335.3 | 243.7 | 8.35 |
| 14 | 4′-$CH_3$CONH | 322.5 | >300 | 9.8 |
| 15 | 4′-Phenyl | 321.5 | 175.7 | 4.7 |

Note:
[a] Absorption maximum wavelength of absorption spectrum determined in methylene chloride.

The second harmonic generation of the 16-(4′-N,N-dimethylaminobenzal)androsta-1,4-diene-3,17-dione obtained by the method of synthesis described above was examined by the powder method. The outline of the powder method is described minutely in Journal of Applied Physics, 36, 3798–3816 (1968). Sample powders graded to particle diameters of 100 μm–125 μm were put between non-fluorescent slide glasses (mfd. by Matsunami Glass Co.) and irradiated by use of a Pulse Nd: YAG Laser (mfd. by Spectron Laser System Co., type SL 303, output 850 mJ, half peak width 15 ns, output per pulse 50 mW, beam diameter 9.5 mm, wavelength 1.064 μm, cycle repetition rate 10 Hz). The intensity of the second harmonic light at 532 nm thus generated was determined by means of a photomultiplier tube through an infrared filter and an UV filter.

EXAMPLES 2-15

Syntheses were conducted in the same manner as in Example 1 except that 788 mg of 4-N,N-dimethylaminobenzaldehyde was replaced by 882 mg of 4-N,N-dimethylamino-2-fluorobenzaldehyde, 1.036 g of 3,4,5-trimethoxybenzaldehyde, 878 mg of 2,3-dimethoxybenzaldehyde, 719 mg of 4-methoxybenzaldehyde, 793 mg of 4-ethoxybenzaldehyde, 866 mg of 4-n-propoxybenzaldehyde, 941 mg of 4-n-butoxybenzaldehyde, 1.121 g of 4-benzyloxybenzaldehyde, 803 mg of 4-methylthiobenzaldehyde, 742 mg of 4-chlorobenzaldehyde, 977 mg of 4-bromobenzaldehyde, 793 mg of 3,4-methylenedioxybenzaldehyde (piperonal), 862 mg of 4-acetamidobenzaldehyde and 962 mg of 4-phenylbenzaldehyde, respectively, to obtain the following compounds:

16-(4'-N,N-dimethylamino-2'-fluorobenzal)androsta-1,4-diene-3,17-dione (compound 2),
16-(3',4',5=-trimethoxybenzal)androsta-1,4-diene-3,7-dione (compound 3),
16-(2',3'-dimethoxybenzal)androsta-1,4-diene-3,17-dione (compound 4),
16-(4'-methoxybenzal)androsta-1,4-diene-3,17-dione (compound 5),
16-(4'-ethoxybenzal)androsta-1,4-diene-3,17-dione (compound 6),
16-(4'-n-propoxybenzal)androsta-1,4-diene-3,17-dione (compound 7),
16-(4'-n-butoxybenzal)androsta-1,4-diene-3,17-dione (compound 8),
16-(4'-benzyloxybenzal)androsta-1,4-diene-3,17-dione (compound 9),
16-(4'-methylthiobenzal)androsta-1,4-diene-3,17-dione (compound 10),
16-(4'-chlorobenzal)androsta-1,4-diene-3,17-dione (compound 11),
16-(4'-bromobenzal)androsta-1,4-diene-3,17-dione (compound 12),
16-(3',4'-methylenedioxybenzal)androsta-1,4-diene-3,17-dione (compound 13),
16-(4'-acetamidobenzal)androsta-1,4-diene-3,17-dione (compound 14), and
16-(4'-phenylbenzal)androsta-1,4-diene-3,17-dione (compound 15).

The ultraviolet-visible region absorption spectra of these compounds are shown in FIGS. 2-15 and the NMR spectra are shown in FIGS. 16-30. The chemical shift values of the representative peaks are collectively shown in Table 2. The absorption maxima, melting points and SHG efficiencies are collectively shown in Table 1.

TABLE 2

(Unit: ppm)

| Compound No. | 18-Methyl | 19-Methyl | $H_1$ | $H_2$ | $H_4$ | $H_{20}$ |
|---|---|---|---|---|---|---|
| Compound 1 | 1.015 | 1.292 | 6.099 | 6.249 | 7.073 | 7.396 |
| Compound 2 | 1.020 | 1.292 | 6.096 | 6.247 | 7.073 | Indistinct |
| Compound 3 | 1.047 | 1.298 | 6.102 | 6.255 | 7.071 | 7.379 |
| Compound 4 | 1.042 | 1.292 | 6.090 | 6.250 | 7.072 | 7.799 |
| Compound 5 | 1.027 | 1.296 | 6.099 | 6.251 | 7.071 | 7.411 |
| Compound 6 | 1.025 | 1.296 | 6.099 | 6.250 | 7.069 | 7.407 |
| Compound 7 | 1.026 | 1.297 | 6.104 | 6.252 | 7.071 | 7.412 |
| Compound 8 | 1.027 | 1.297 | 6.102 | 6.253 | 7.072 | 7.411 |
| Compound 9 | 1.024 | 1.293 | 6.101 | 6.252 | 7.067 | Indistinct |
| Compound 10 | 1.031 | 1.296 | 6.101 | 6.252 | 7.069 | Indistinct |
| Compound 11 | 1.037 | 1.298 | 6.101 | 6.253 | 7.067 | Indistinct |
| Compound 12 | 1.036 | 1.298 | 6.101 | 6.253 | 7.067 | Indistinct |
| Compound 13 | 1.024 | 1.297 | 6.104 | 6.258 | 7.071 | 7.367 |
| Compound 14 | 0.989 | 1.295 | 6.004 | 6.138 | 7.143 | 7.262 |
| Compound 15 | 1.054 | 1.302 | 6.106 | 6.257 | 7.071 | Indistinct |

FIG. 1 shows the ultraviolet-visible region absorption spectrum of the methylene chloride solution of the compound 1 obtained in Example.

Figure 2:
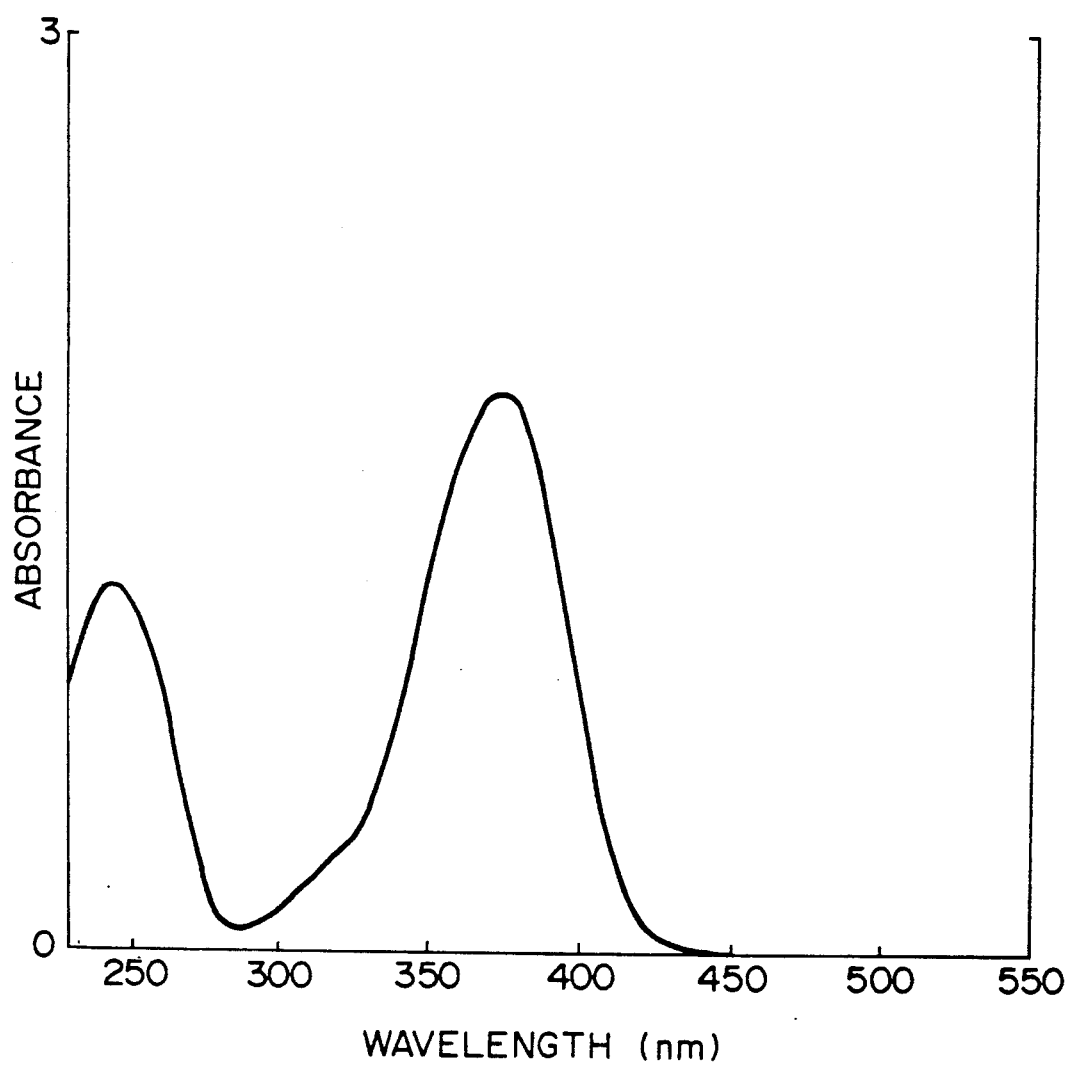

FIG. 2 shows the ultraviolet-visible region absorption spectrum of the methylene chloride solution of the compound 2 obtained in Example.

Figure 3:
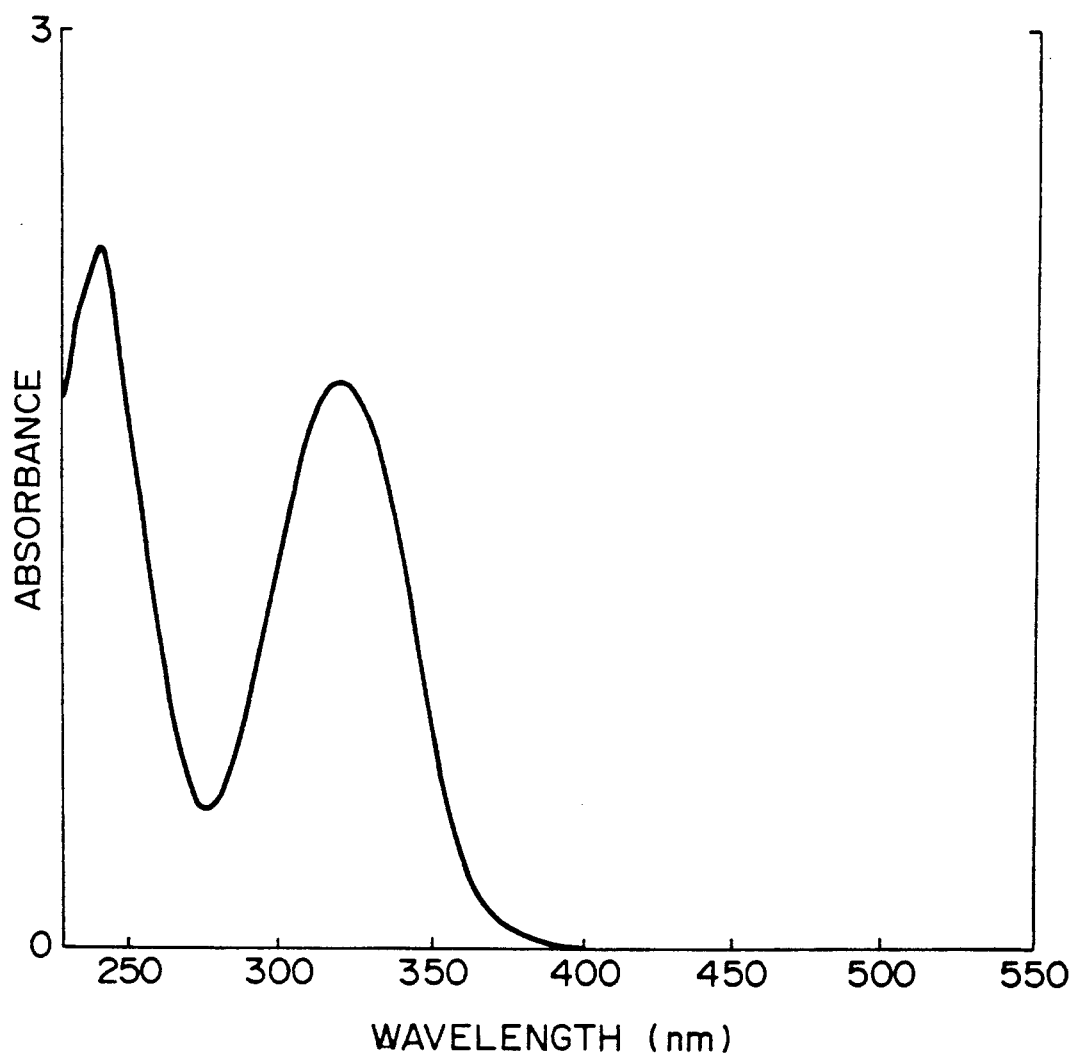

FIG. 3 shows the ultraviolet-visible region absorption spectrum of the methylene chloride solution of the compound 3 obtained in Example.

Figure 4:
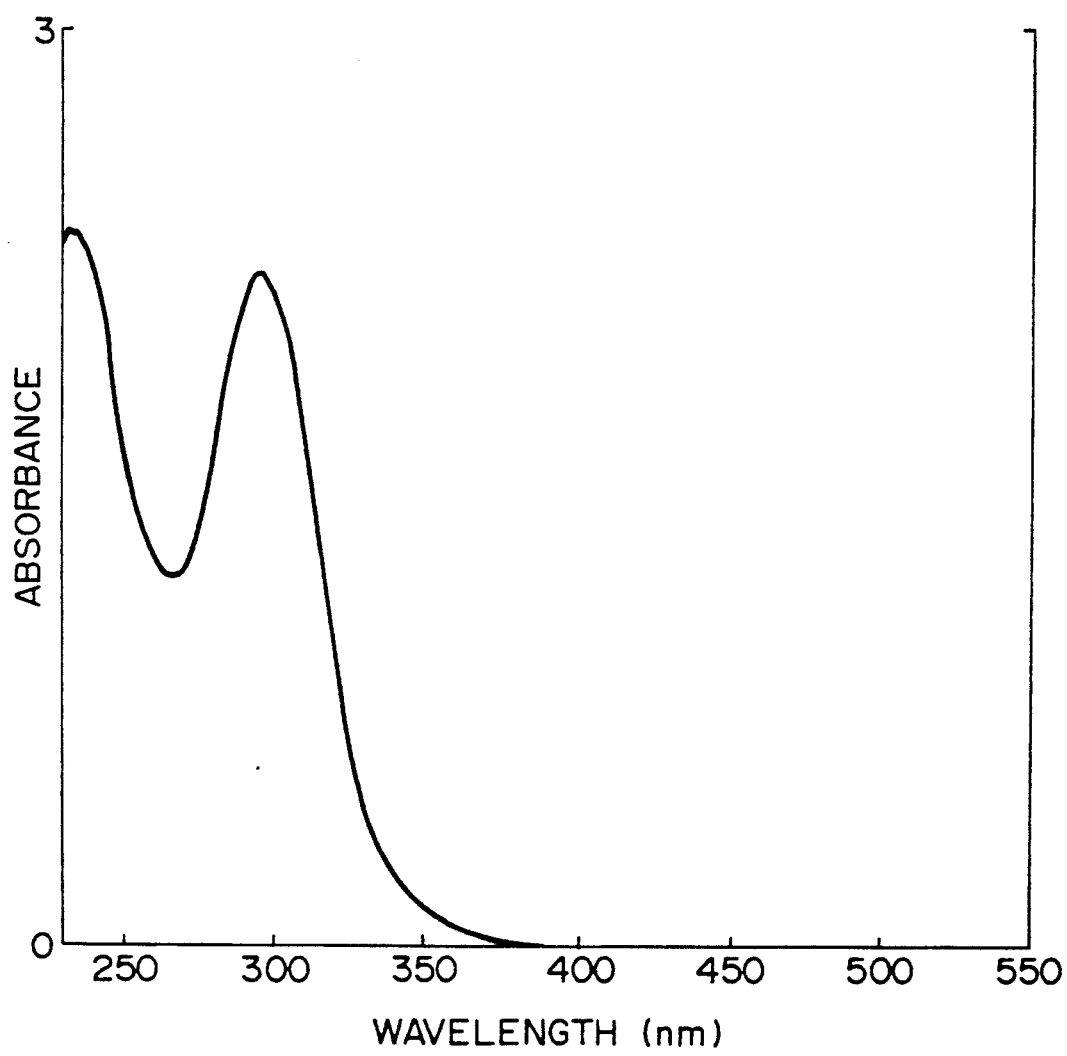

FIG. 4 shows the ultraviolet-visible region absorption spectrum of the methylene chloride solution of the compound 4 obtained in Example.

Figure 5:
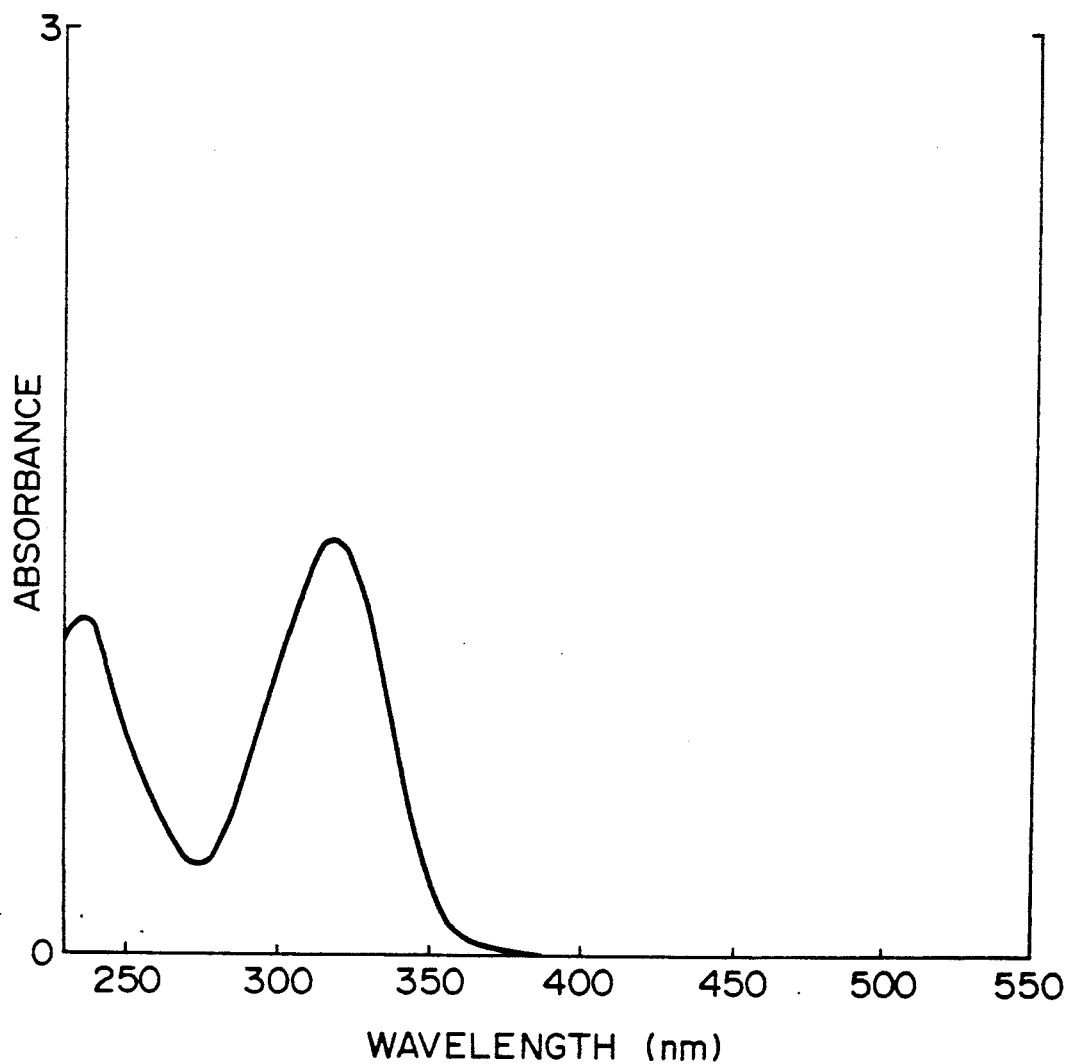

FIG. 5 shows the ultraviolet-visible region absorption spectrum of the methylene chloride solution of the compound 5 obtained in Example.

FIG. 6 shows the ultraviolet-visible region absorption spectrum of the methylene chloride solution of the compound 6 obtained in Example.

Figure 7:
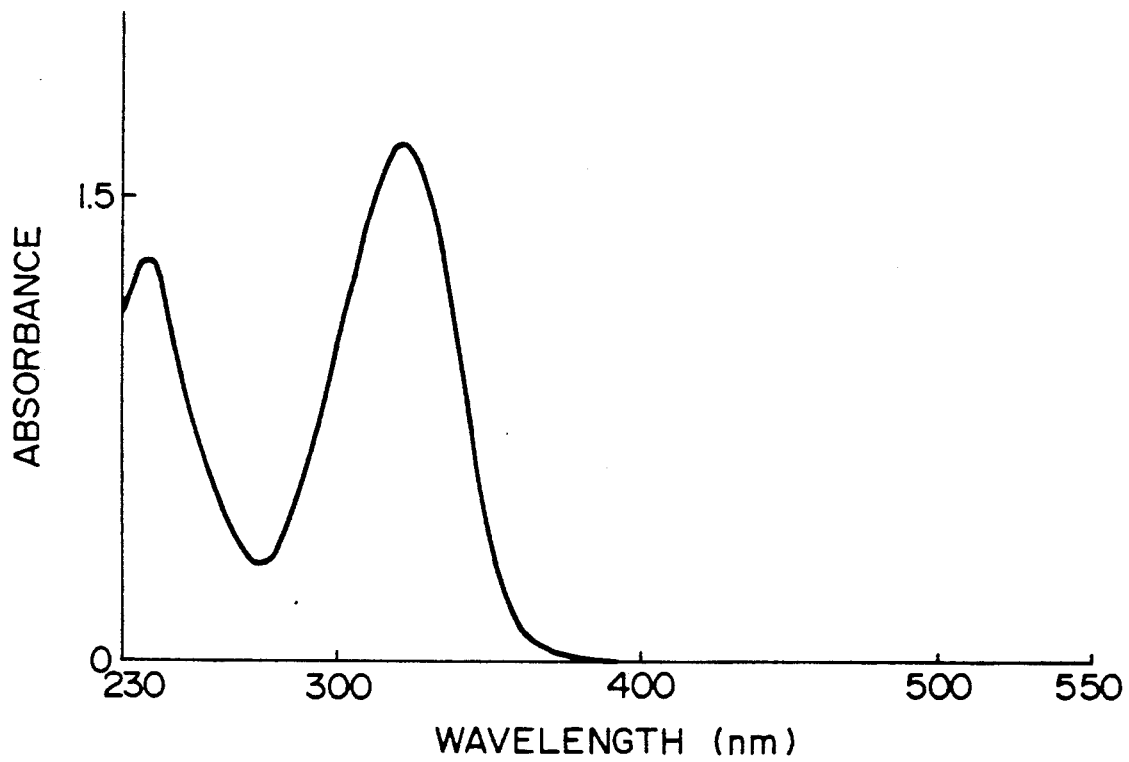

FIG. 7 shows the ultraviolet-visible region absorption spectrum of the methylene chloride solution of the compound 7 obtained in Example.

Figure 8:
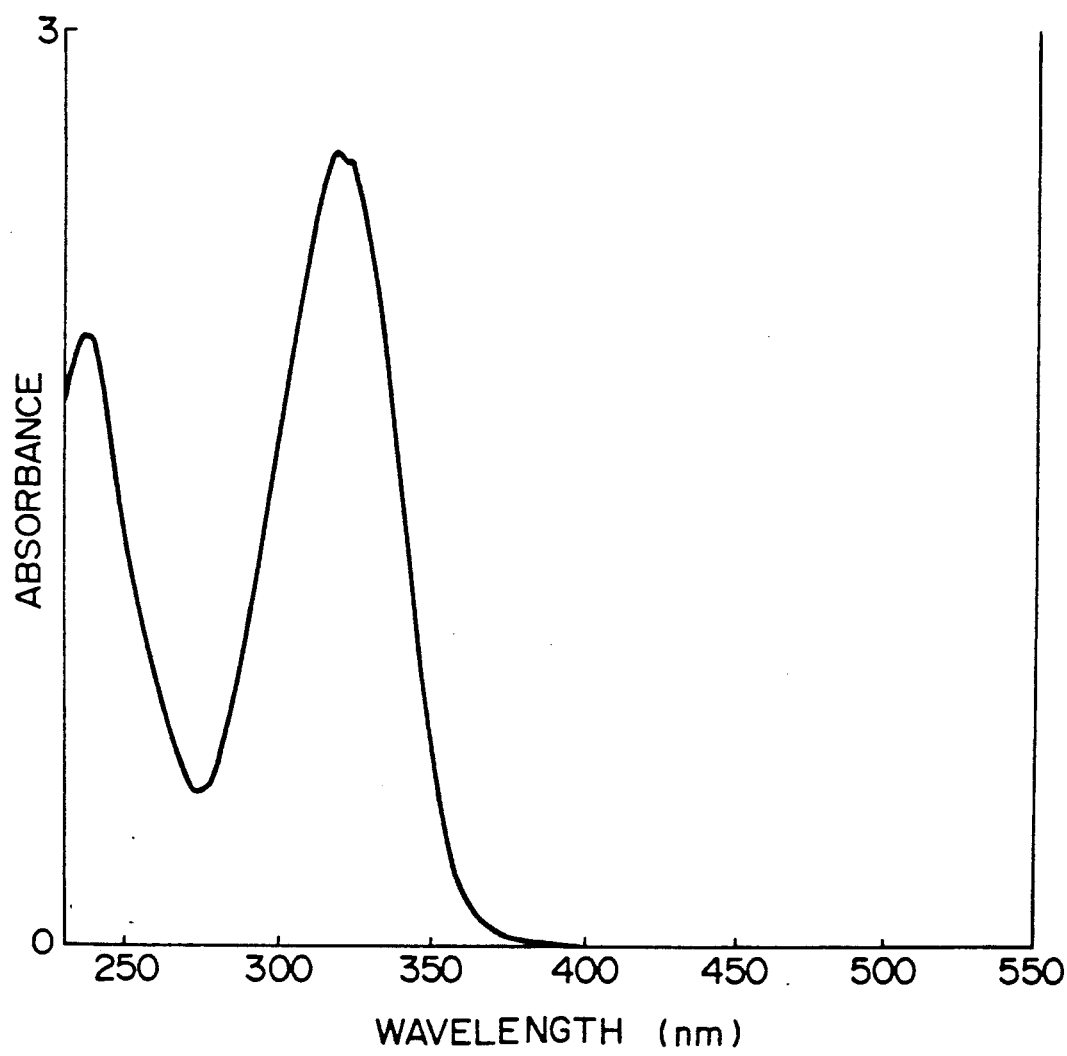

FIG. 8 shows the ultraviolet-visible region absorption spectrum of the methylene chloride solution of the compound 8 obtained in Example.

Figure 9:
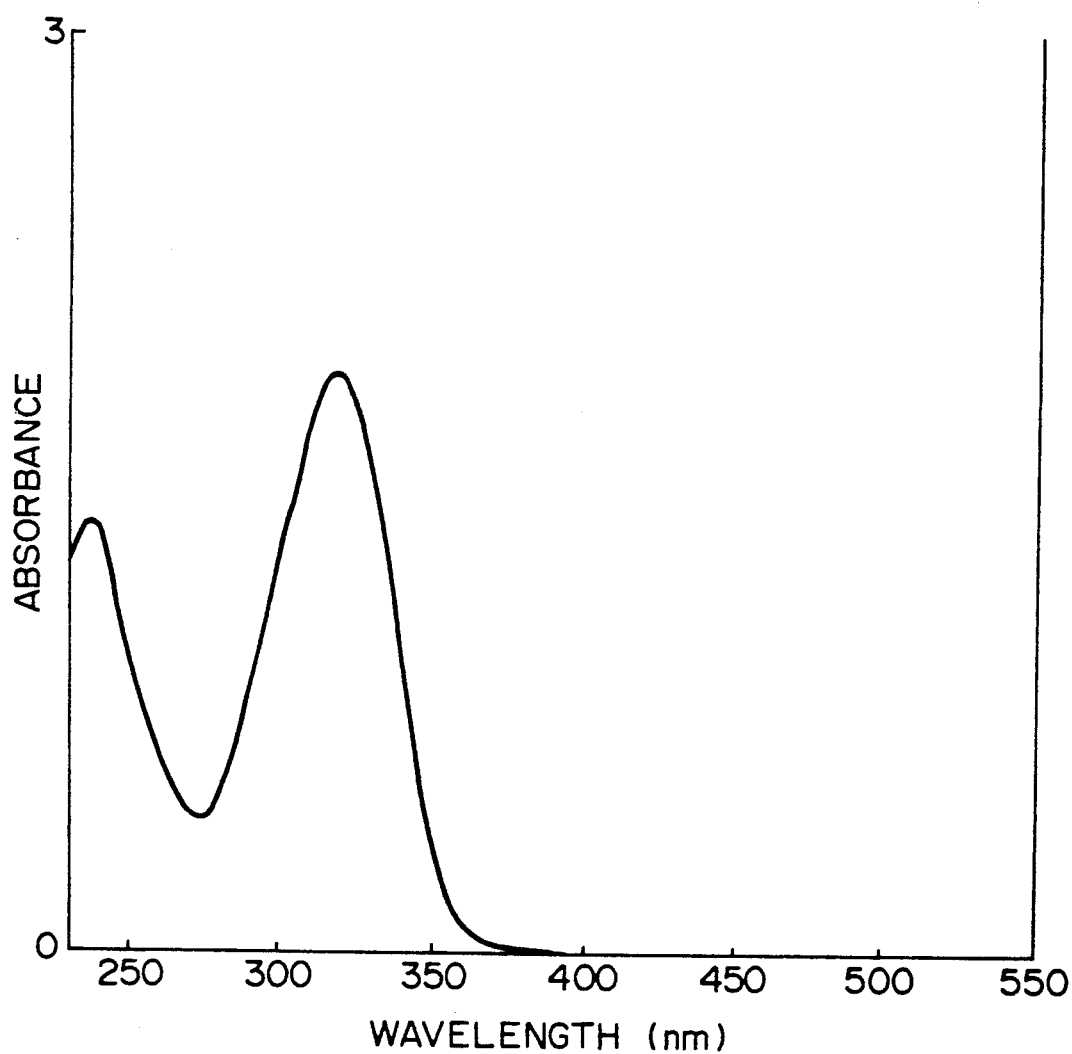

FIG. 9 shows the ultraviolet-visible region absorption spectrum of the methylene chloride solution of the compound 9 obtained in Example.

Figure 10:
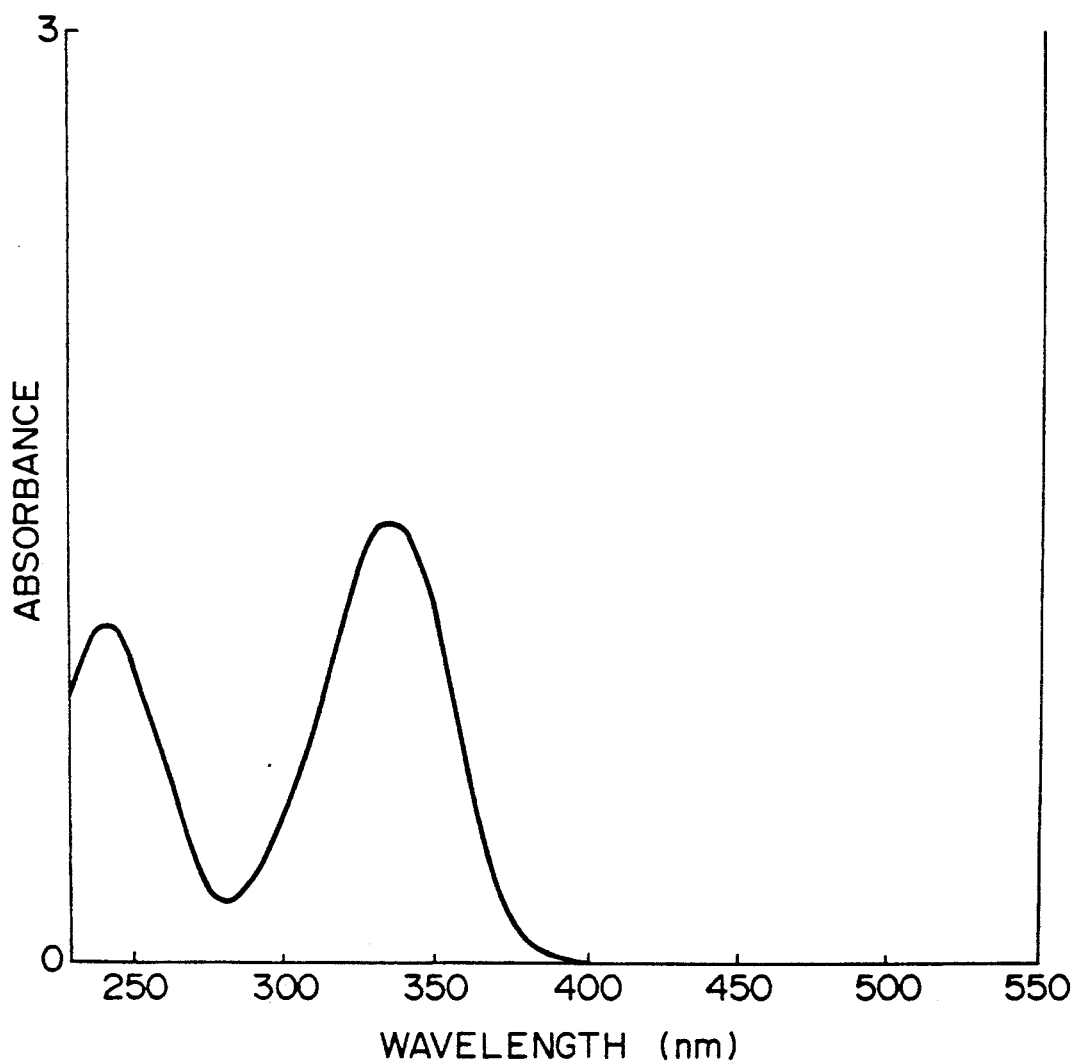

FIG. 10 shows the ultraviolet-visible region absorption spectrum of the methylene chloride solution of the compound 10 obtained in Example.

Figure 11:
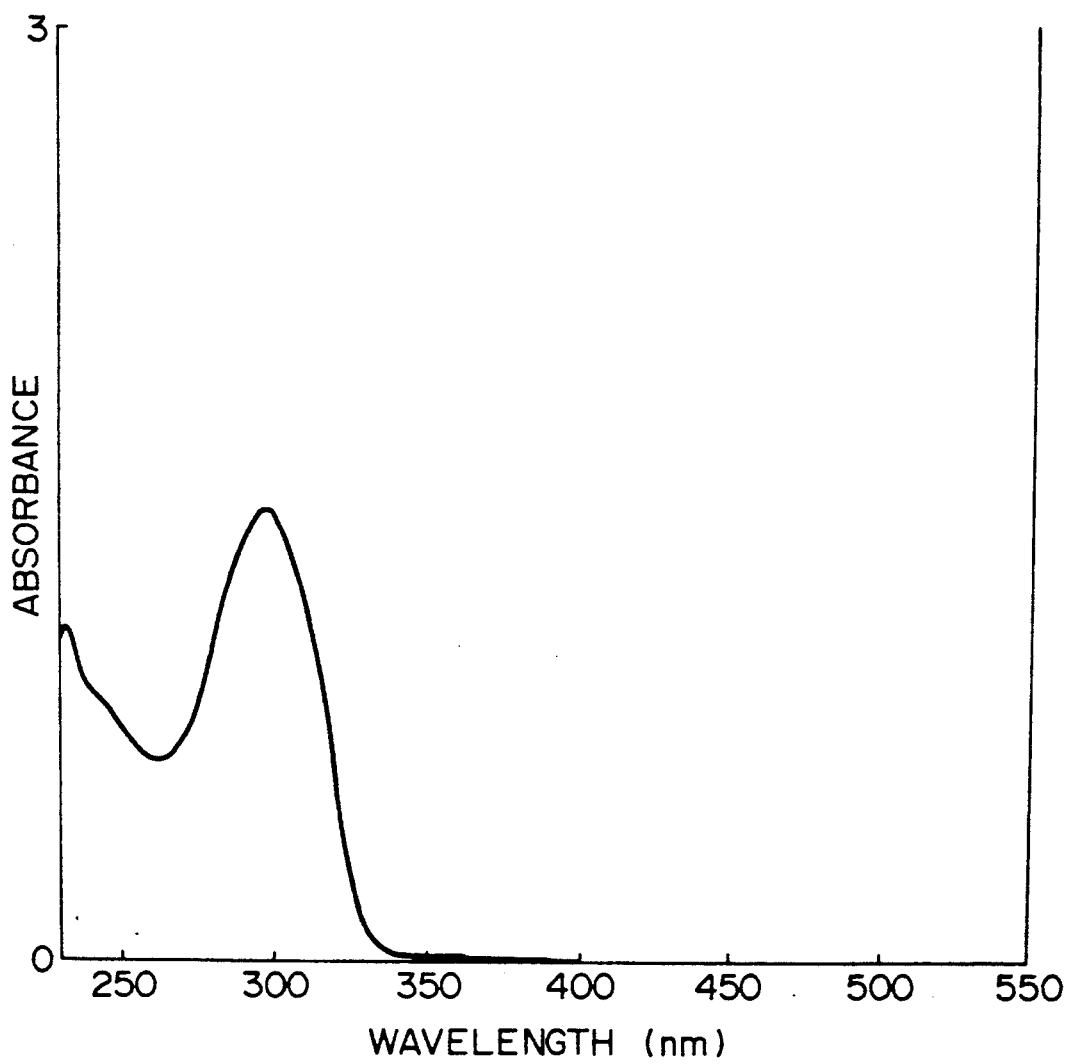

FIG. 11 shows the ultraviolet-visible region absorption spectrum of the methylene chloride solution of the compound 11 obtained in Example.

Figure 12:
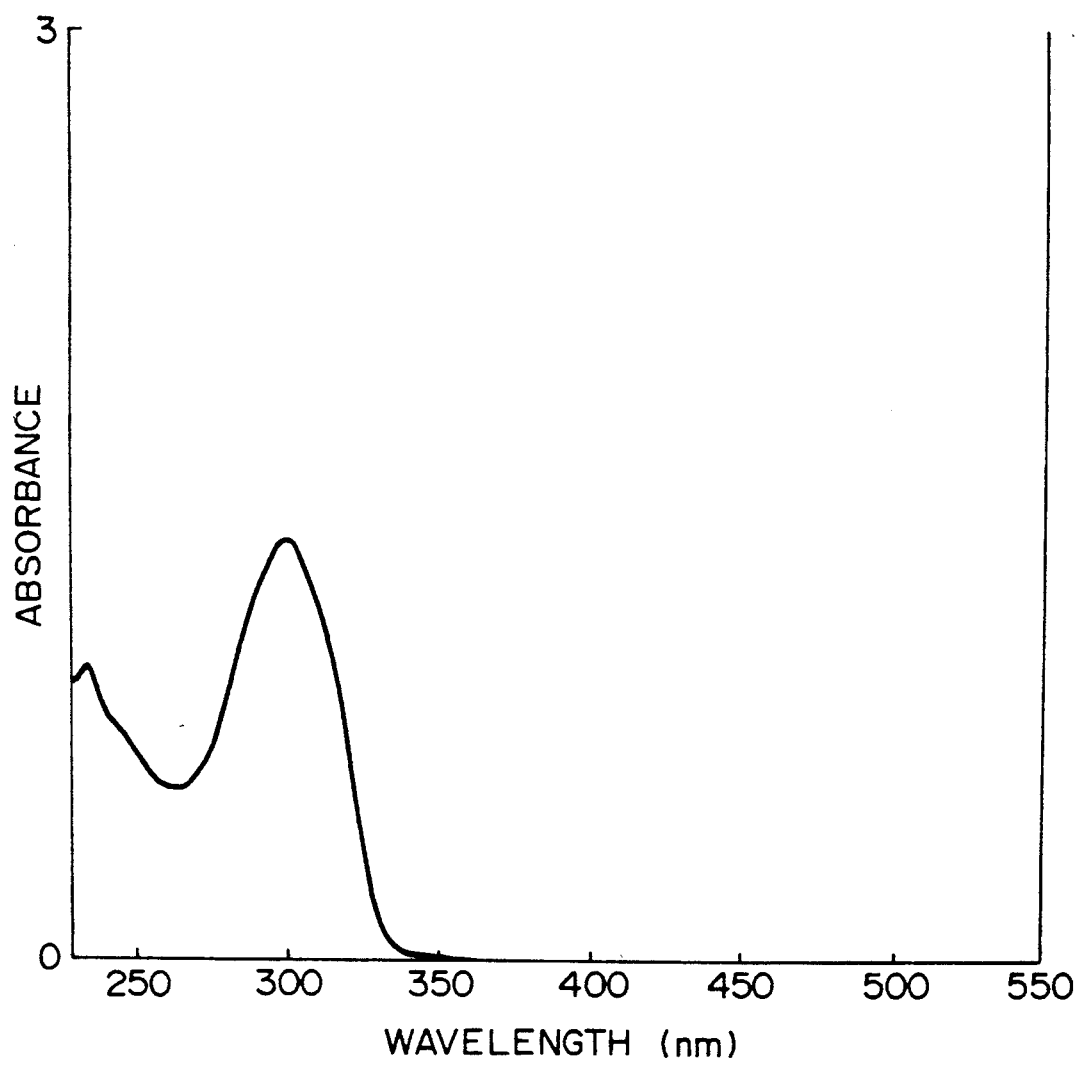

FIG. 12 shows the ultraviolet-visible region absorption spectrum of the methylene chloride solution of the compound 12 obtained in Example.

Figure 13:
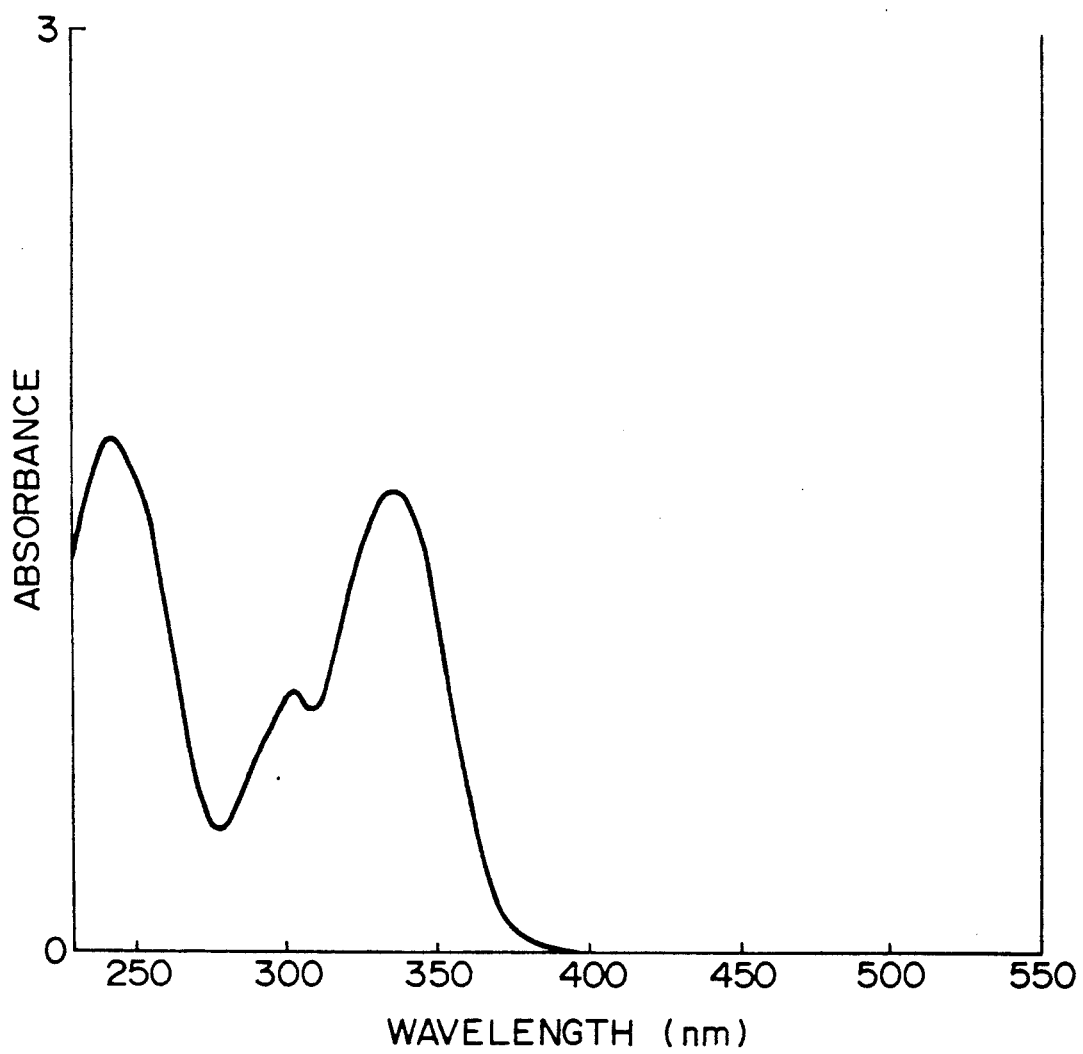

FIG. 13 shows the ultraviolet-visible region absorption spectrum of the methylene chloride solution of the compound 13 obtained in Example.

Figure 14:
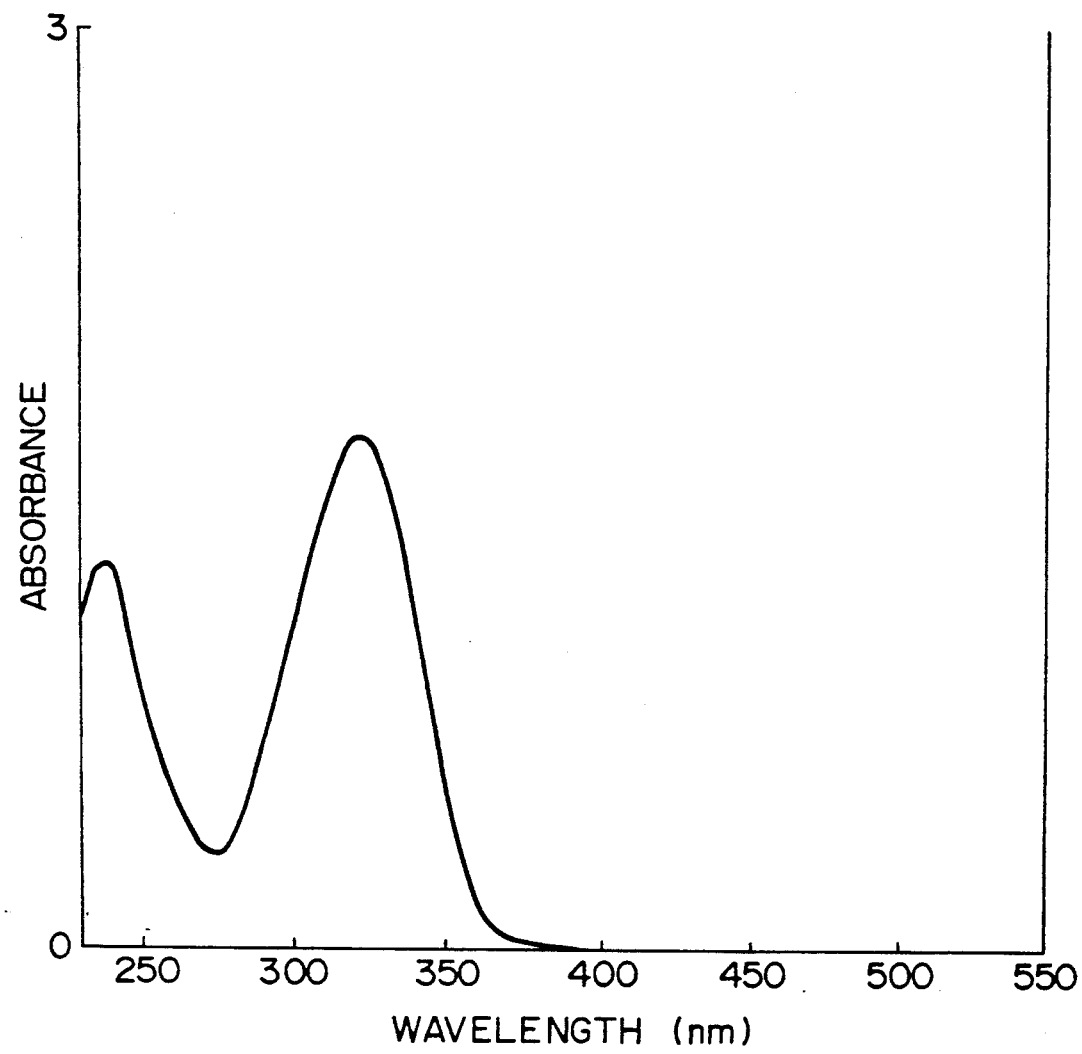

FIG. 14 shows the ultraviolet-visible region absorption spectrum of the methylene chloride solution of the compound 14 obtained in Example.

Figure 15:
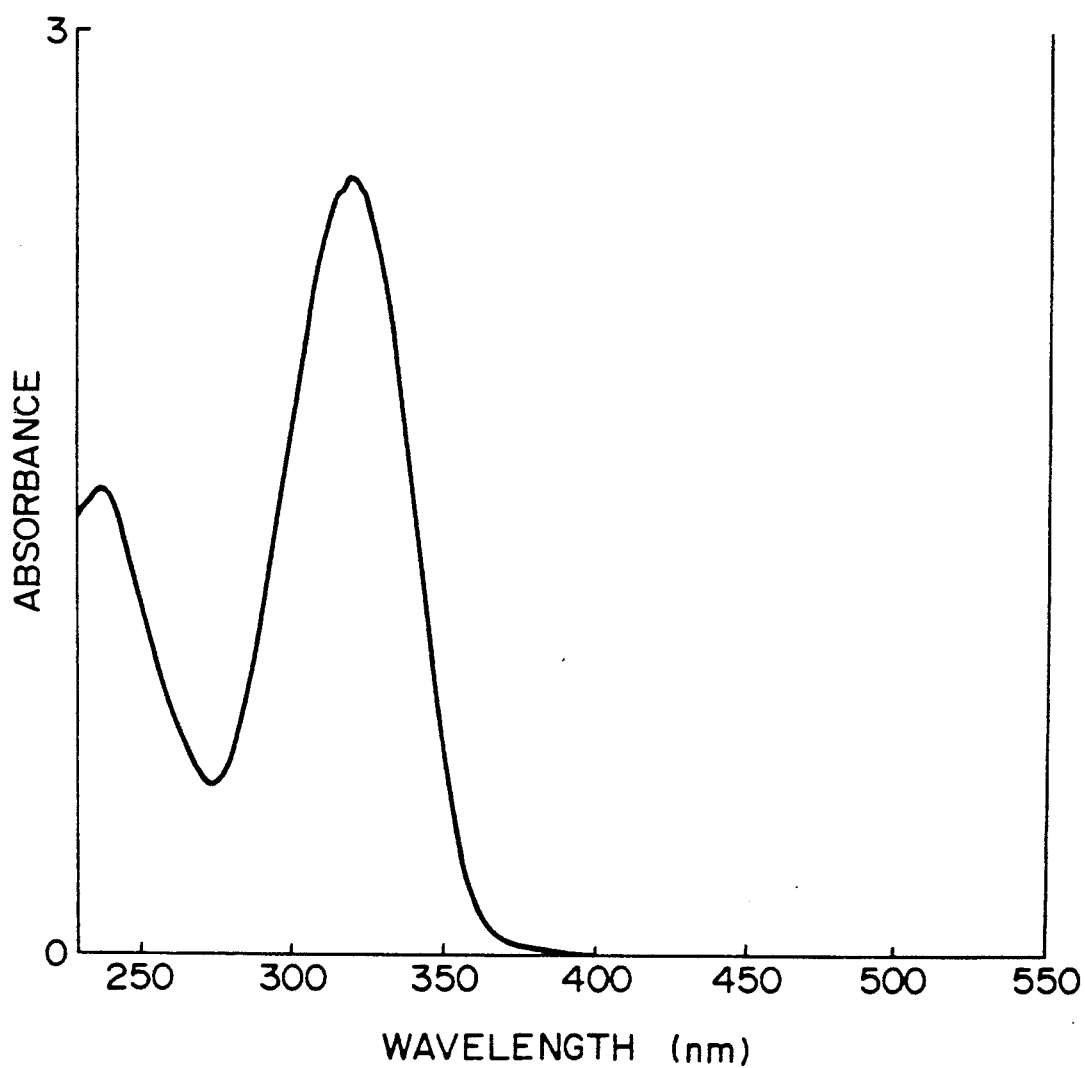

FIG. 15 shows the ultraviolet-visible region absorption spectrum of the methylene chloride solution of the compound 15 obtained in Example.

Figure 16:
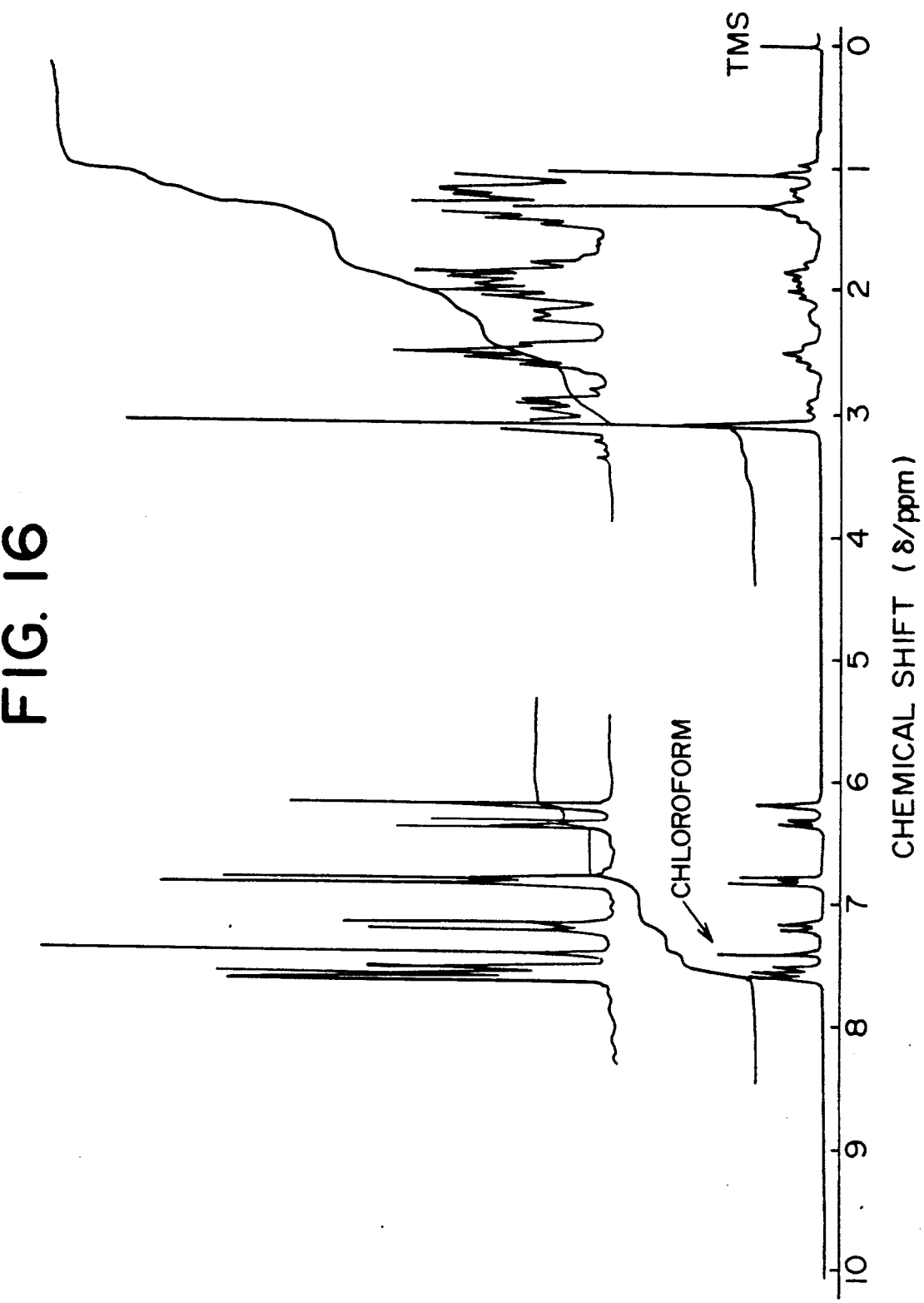
FIGS. 16 to 30 are NMR spectra of compounds of the formula [I] in $d_1$-chloroform.

FIG. 16 shows the NMR spectrum of the heavy chloroform solution of the compound 1 obtained in Example.

Figure 17:
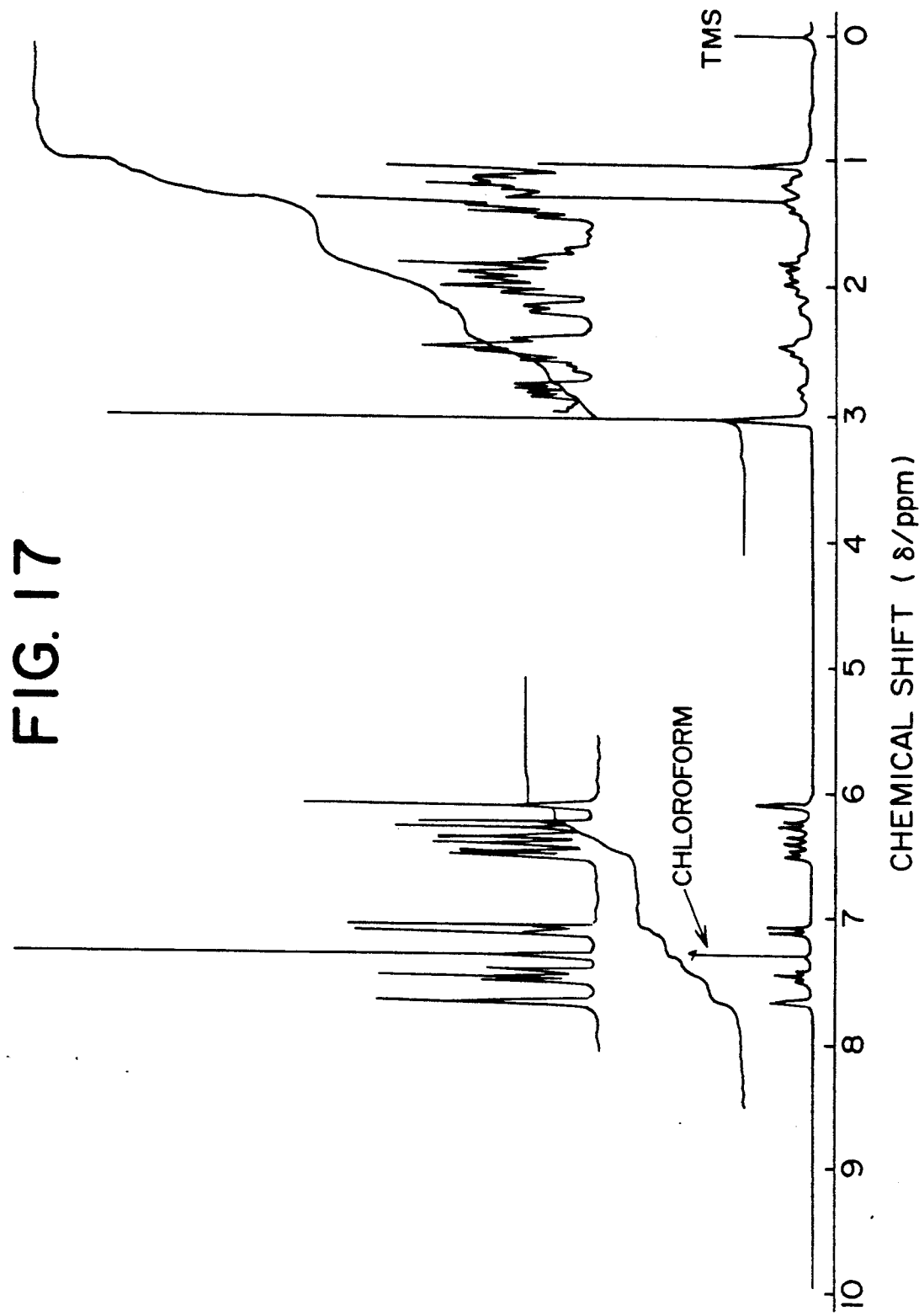

FIG. 17 shows the NMR spectrum of the heavy chloroform solution of the compound 2 obtained in Example.

Figure 18:
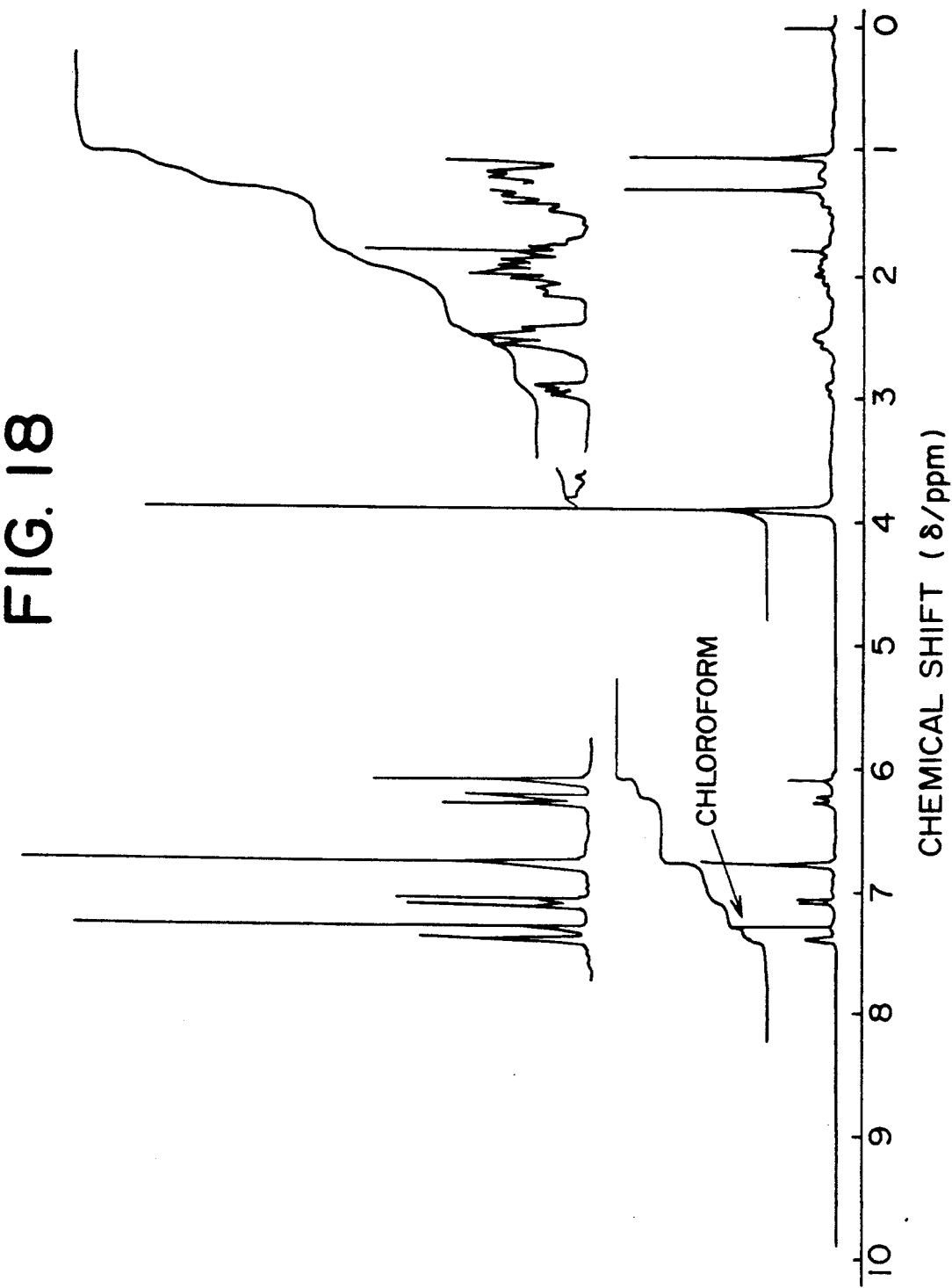

FIG. 18 shows the NMR spectrum of the heavy chloroform solution of the compound 3 obtained in Example.

Figure 19:
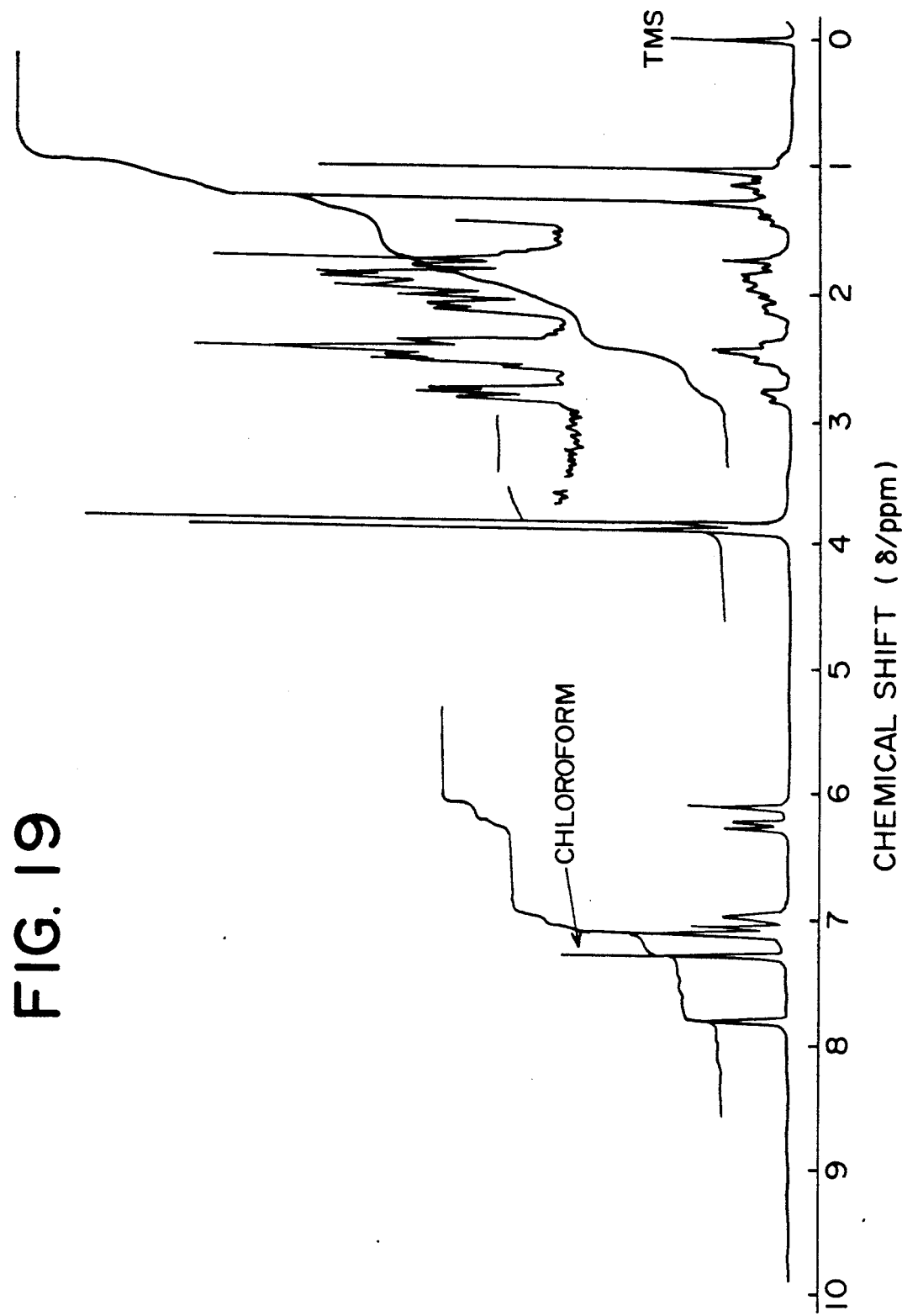

FIG. 19 shows the NMR spectrum of the heavy chloroform solution of the compound 4 obtained in Example.

Figure 20:
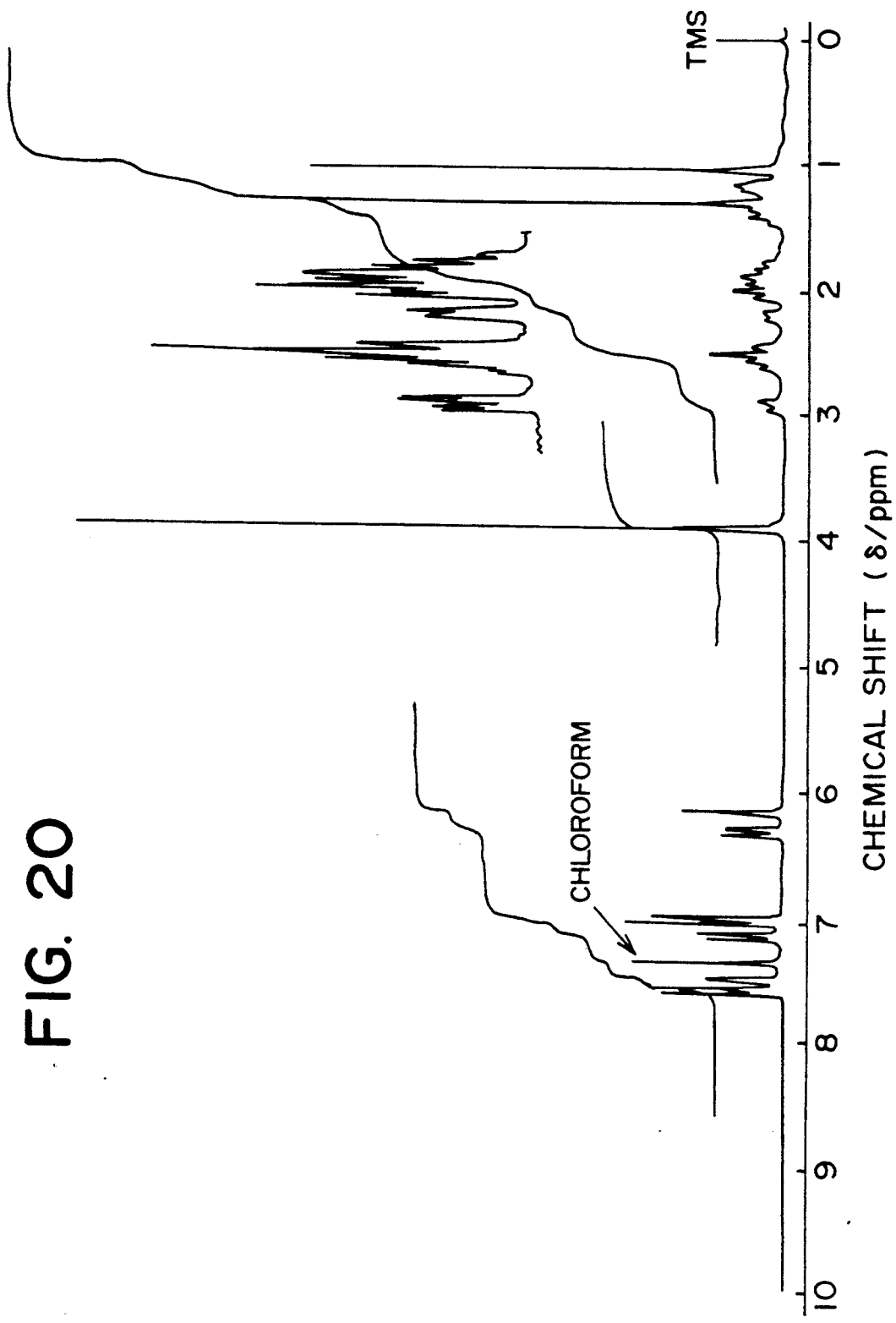

FIG. 20 shows the NMR spectrum of the heavy chloroform solution of the compound 5 obtained in Example.

Figure 21:
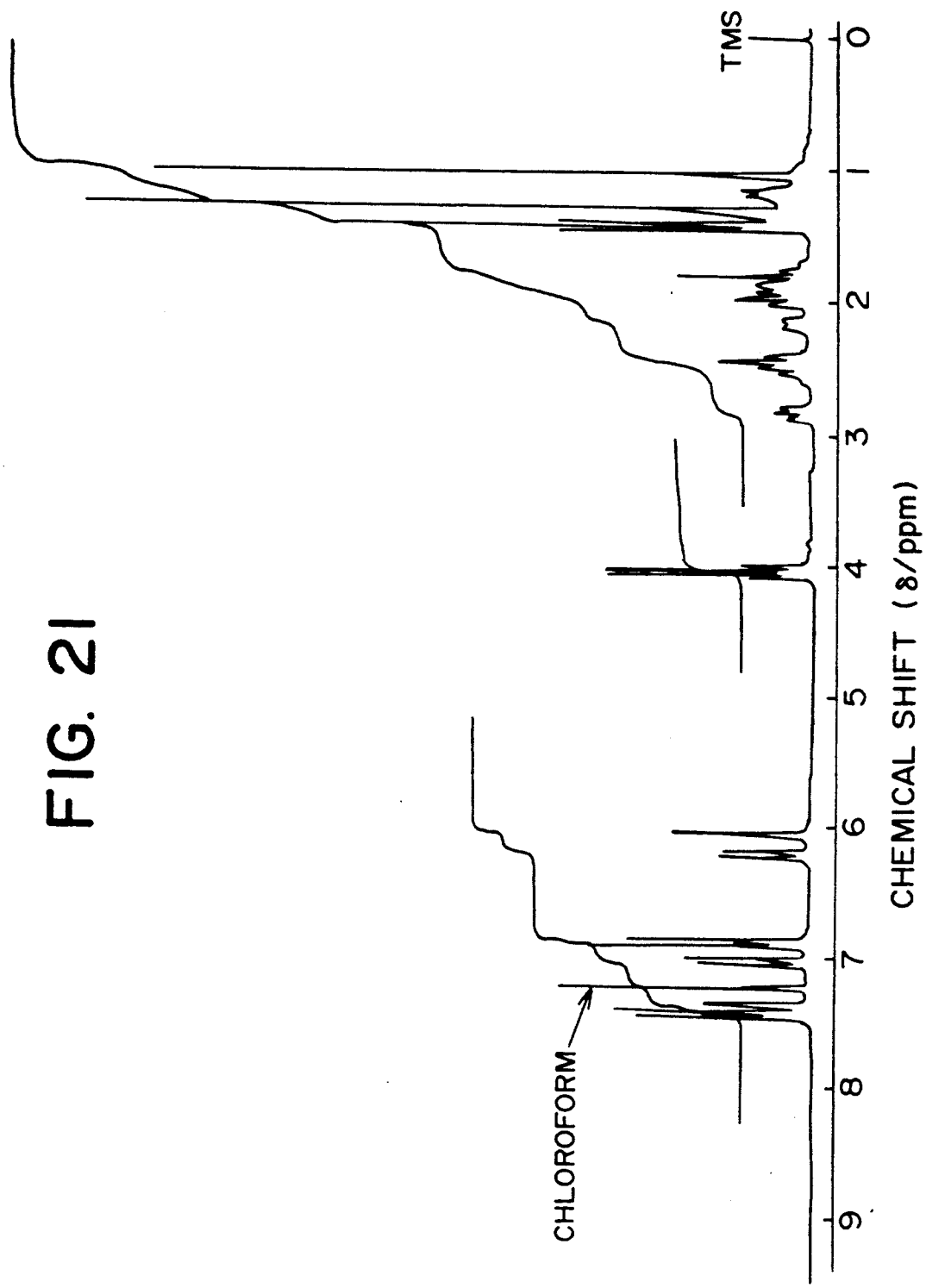

FIG. 21 shows the NMR spectrum of the heavy chloroform solution of the compound 6 obtained in Example.

Figure 22:
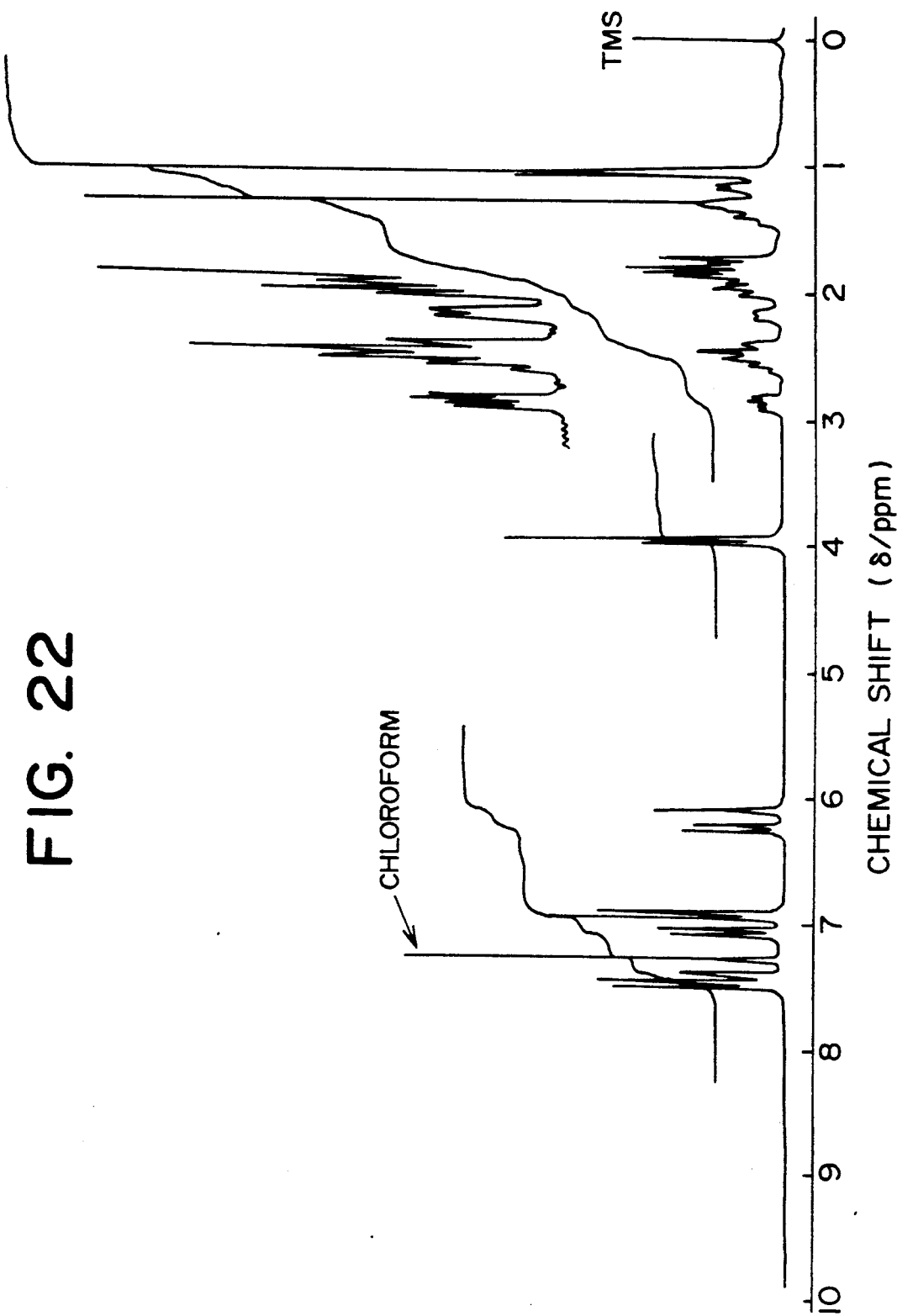

FIG. 22 shows the NMR spectrum of the heavy chloroform solution of the compound 7 obtained in Example.

Figure 23:
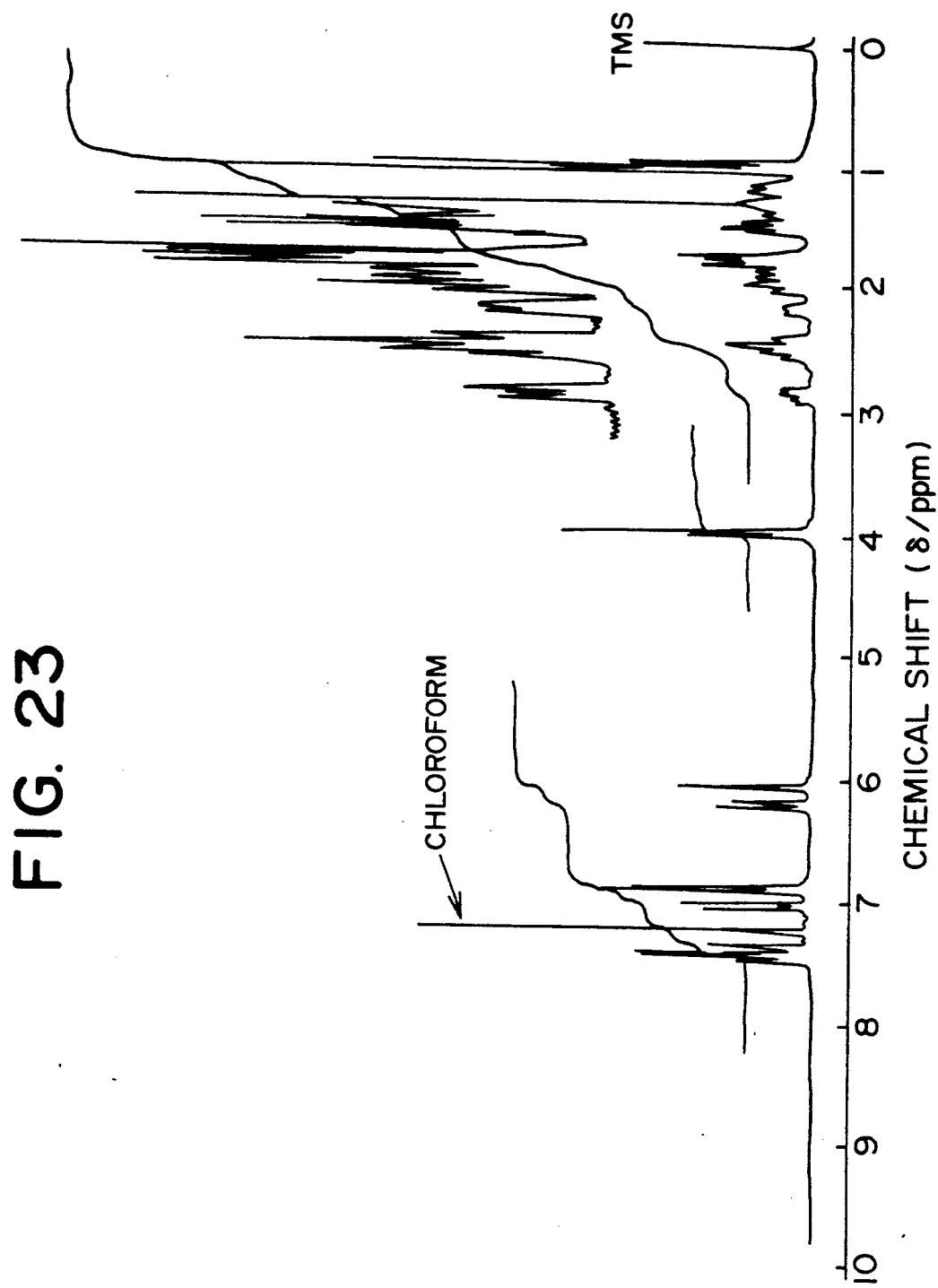

FIG. 23 shows the NMR spectrum of the heavy chloroform solution of the compound 8 obtained in Example.

Figure 24:
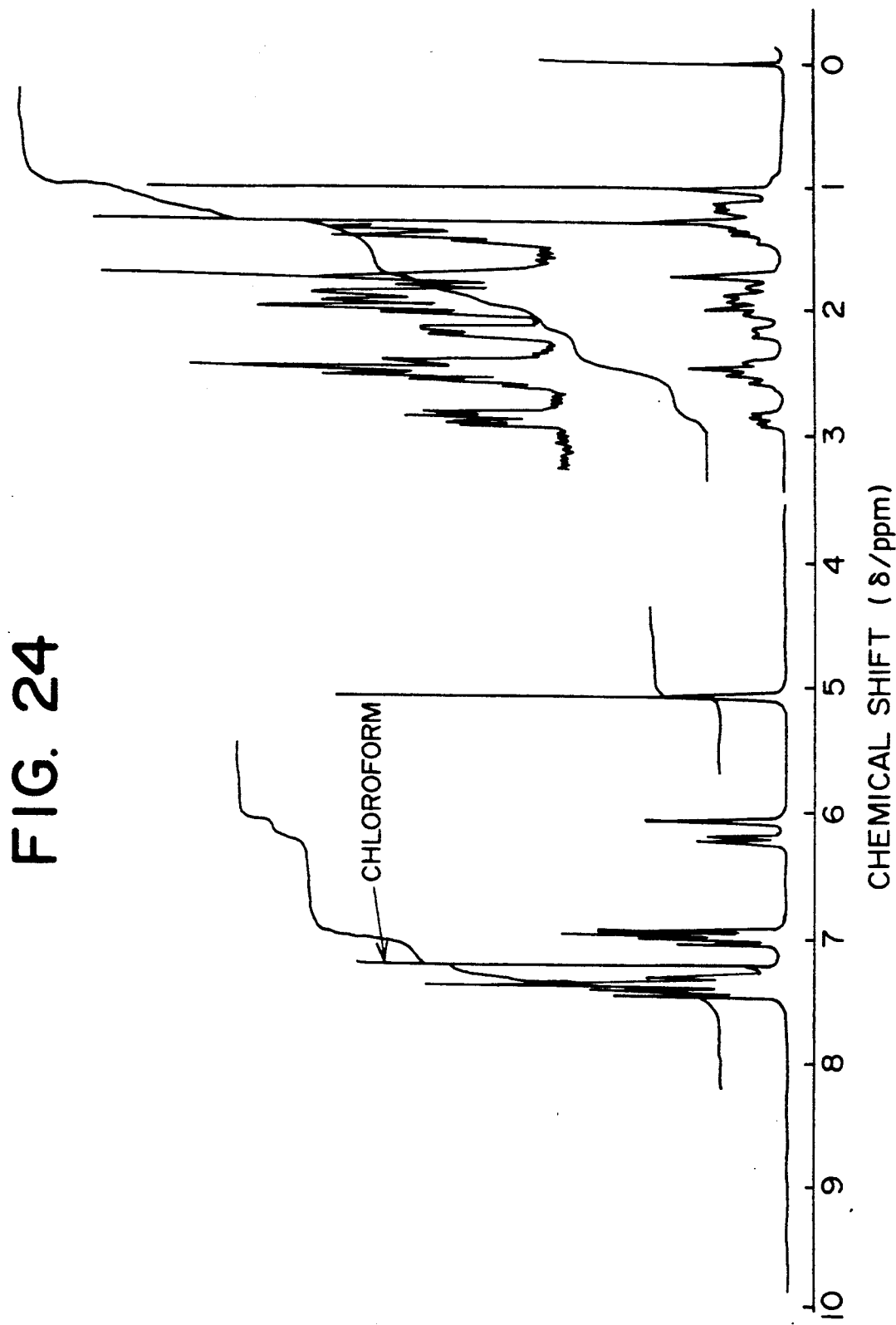

FIG. 24 shows the NMR spectrum of the heavy chloroform solution of the compound 9 obtained in Example.

Figure 25:
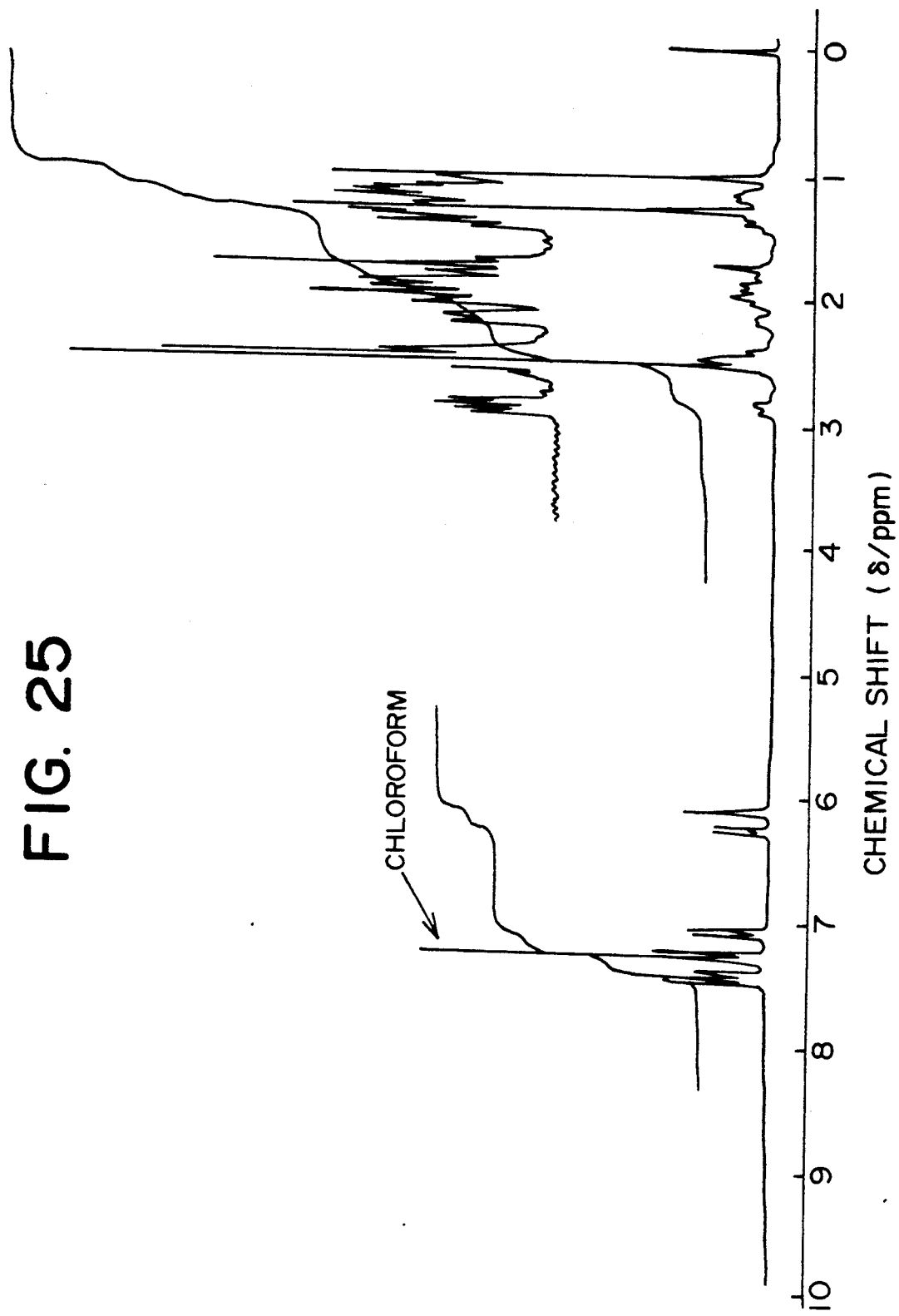

FIG. 25 shows the NMR spectrum of the heavy chloroform solution of the compound 10 obtained in Example.

Figure 26:
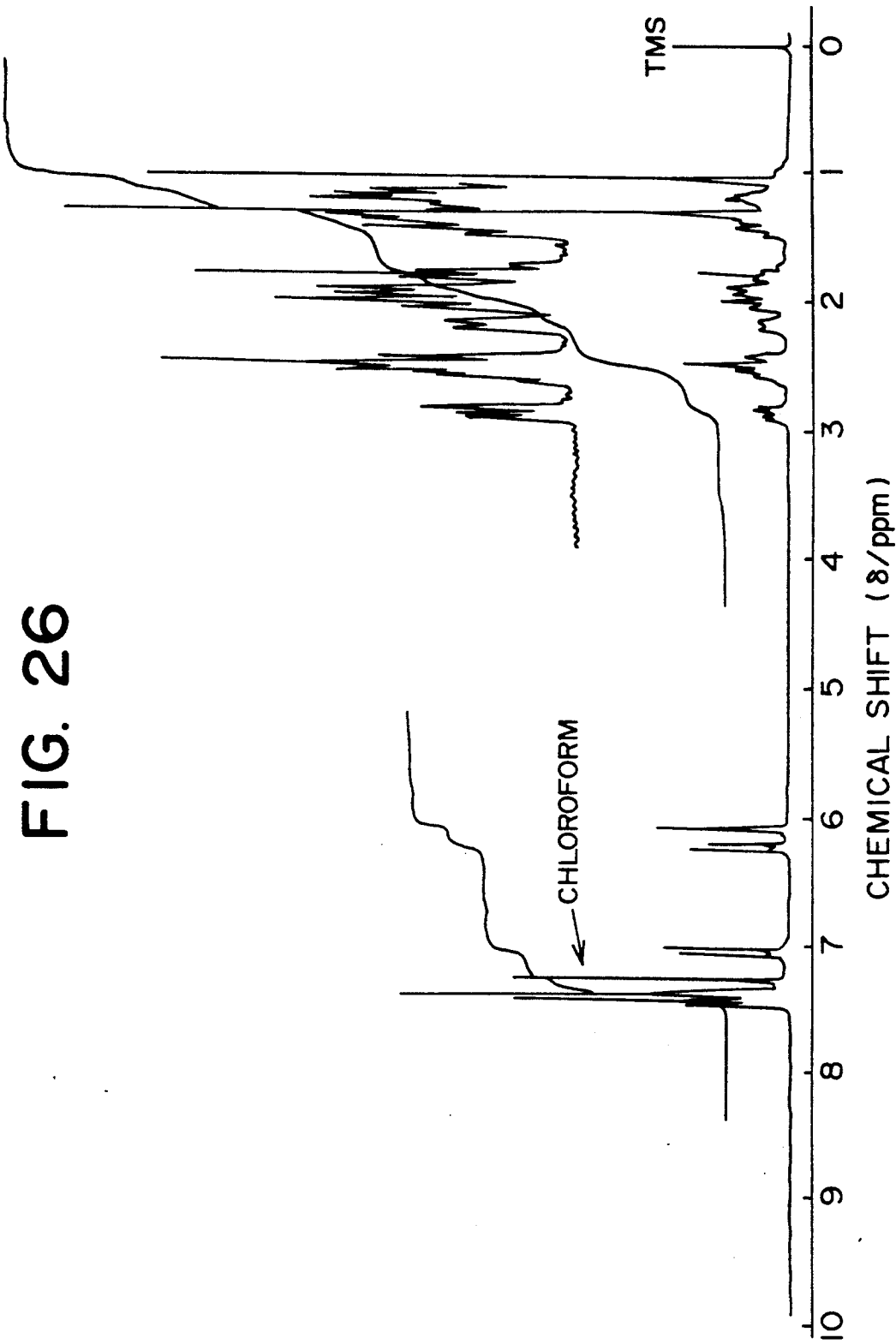

FIG. 26 shows the NMR spectrum of the heavy chloroform solution of the compound 11 obtained in Example.

Figure 27:
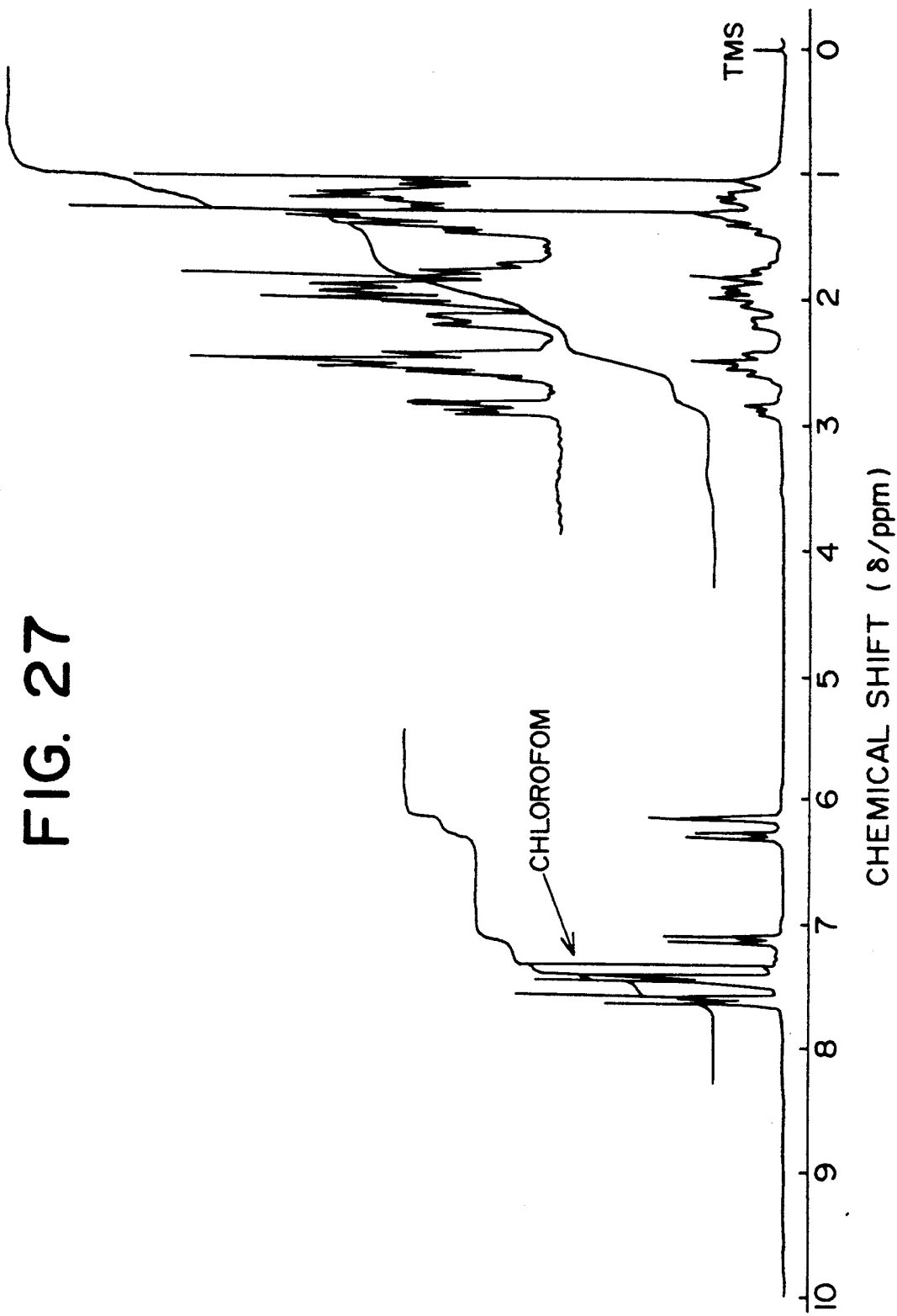

FIG. 27 shows the NMR spectrum of the heavy chloroform solution of the compound 12 obtained in Example.

Figure 28:
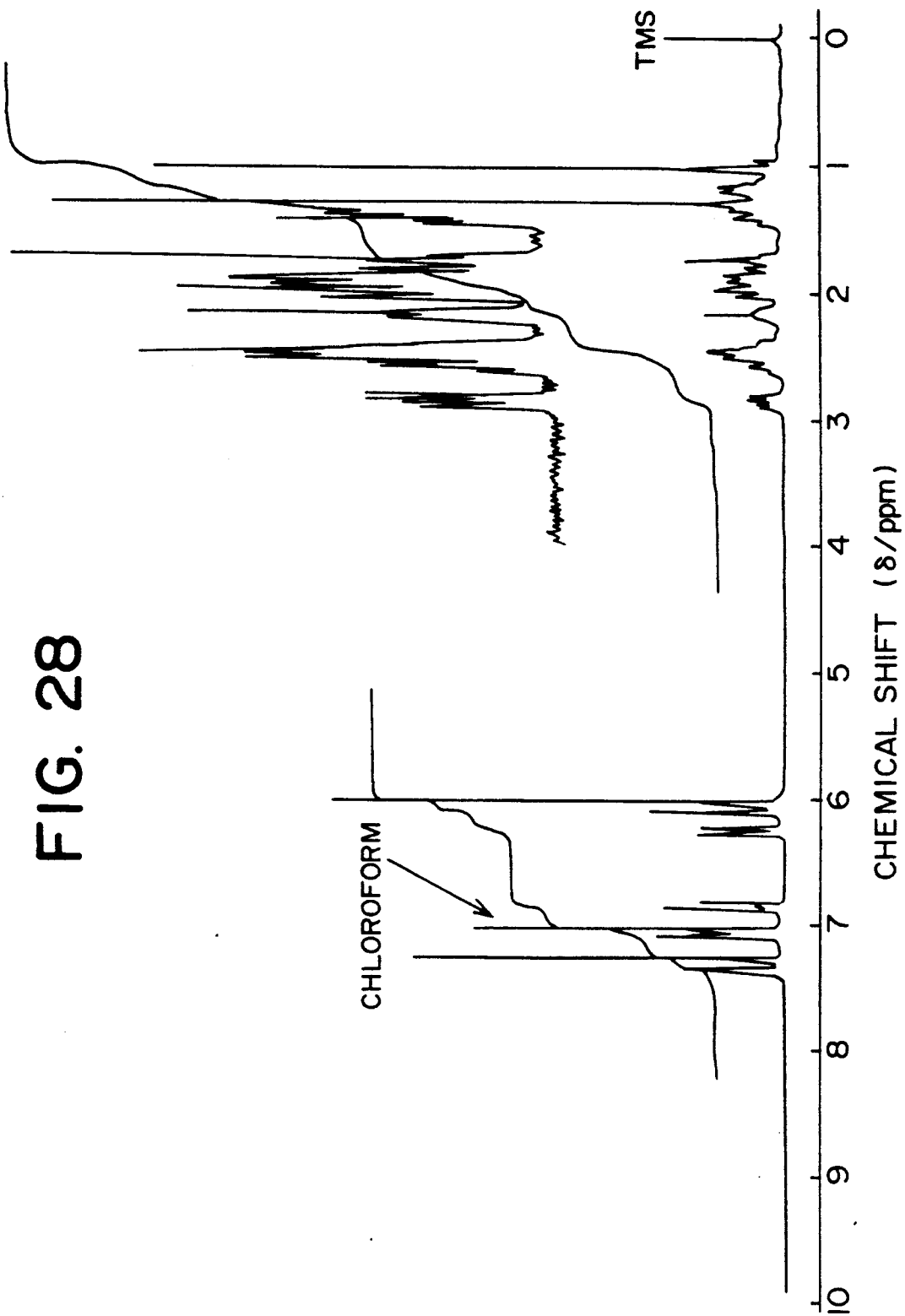

FIG. 28 shows the NMR spectrum of the heavy chloroform solution of the compound 13 obtained in Example.

Figure 29:
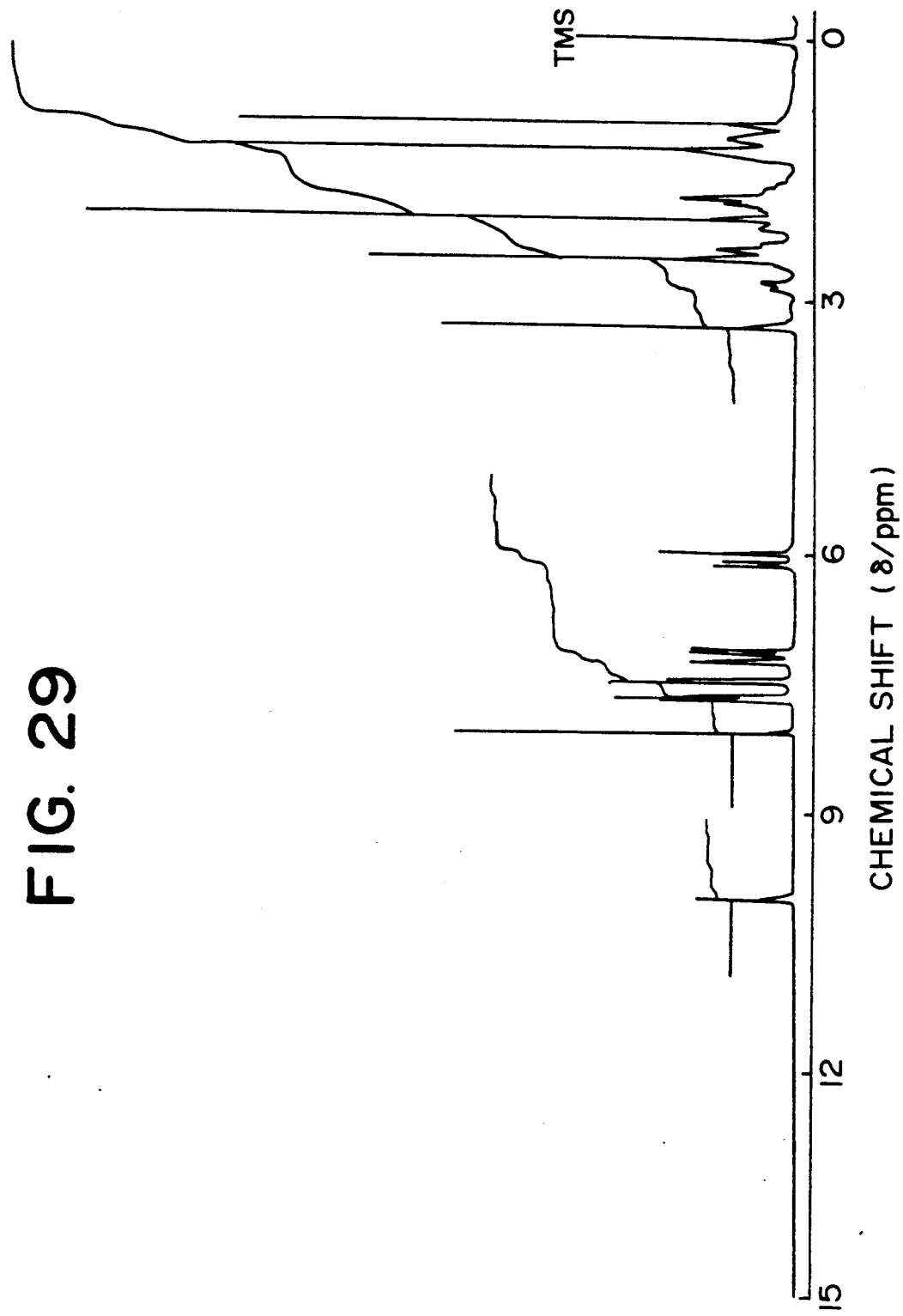

FIG. 29 shows the NMR spectrum of the heavy chloroform solution of the compound 14 obtained in Example.

Figure 30:
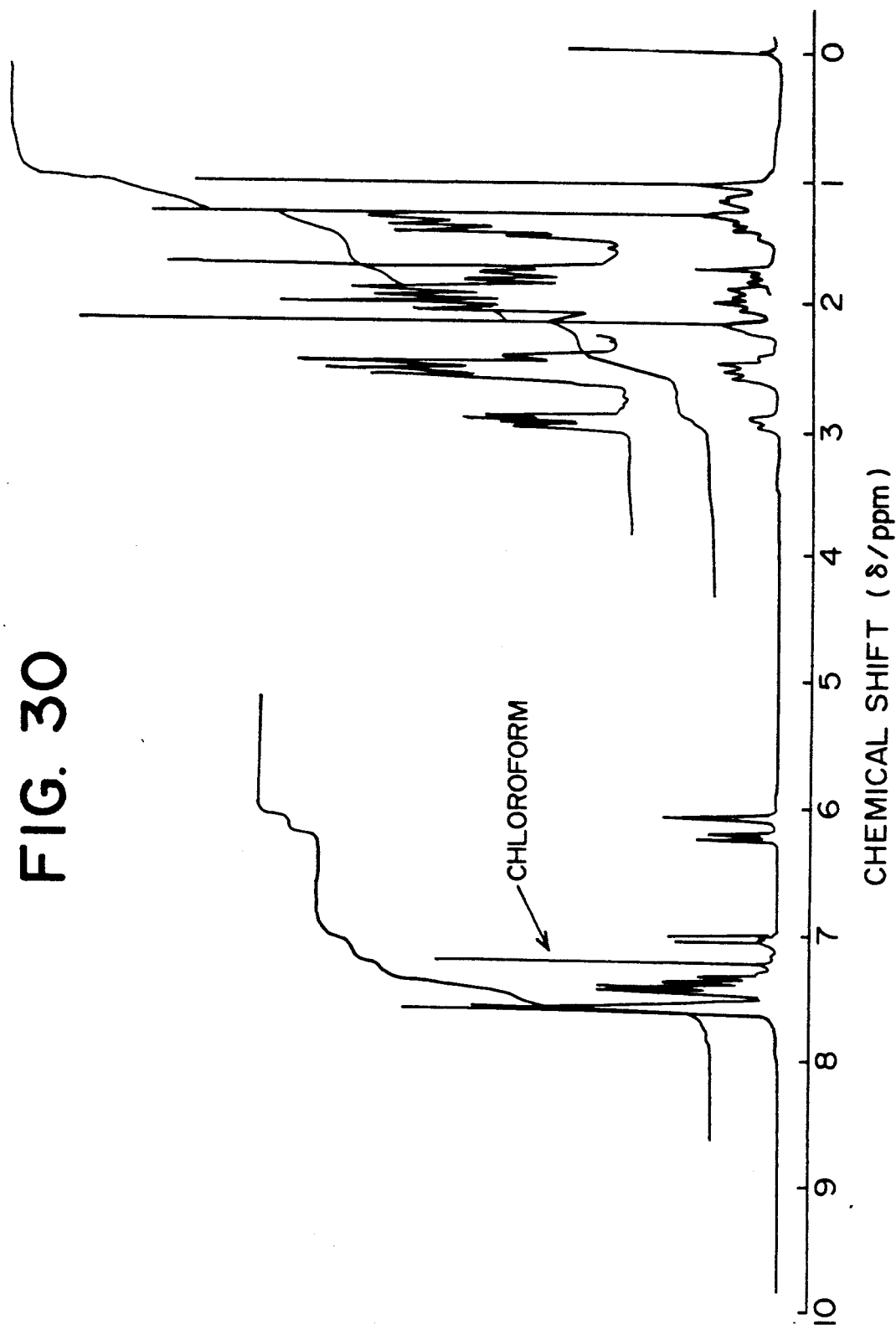

FIG. 30 shows the NMR spectrum of the heavy chloroform solution of the compound 15 obtained in Example.

The 16-benzalandrosta-1,4-diene-3,17-dione compound of the present invention has a high wavelength conversion efficiency and an excellent transparency in the visible region which is necessary for a wavelength conversion material. Accordingly, non-linear optical materials which have a high non-linear optical coefficient and non-linear optical components which have a high non-linear optical effect can be obtained from the compounds of the formula [I].

What is claimed is:

1. A 16-benzalandrosta-1,4-diene-3,17-dione compound represented by the formula:

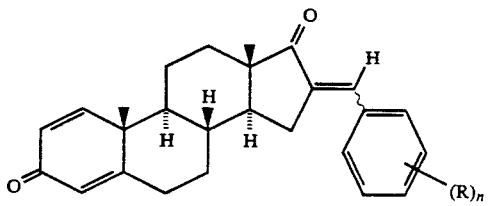

wherein R is a hydrogen, chlorine, bromine or fluorine atom, an alkyl group having 1-10 carbon atoms, an alkoxy group having 1-10 carbon atoms, an acetamido group having 1-10 carbon atoms, an aryl group having 6-10 carbon atoms, an alkylthio group having 1-10 carbon atoms, an aryloxy group having 6-10 carbon atoms, an arylthio group having 6-10 carbon atoms, an aralkyloxy group having 7-11 carbon atoms, or a mono- or dialkylamino group having 1-20 carbon atoms; n is an integer of 1 to 5, provided that when n is 2 or more, each R may be the same as or different from each other and the adjacent substituents may conjointly form a ring; and the bond shown by a wavy pattern indicates a cis- or trans- position.

2. A compound according to claim 1, which is 16-(4'-methoxybenzal)androsta-1,4-diene-3,17-dione.

3. A compound according to claim 1, which is 16-(4'-methylthiobenzal)androsta-1,4-diene-3,17-dione.

4. A compound according to claim 1, which is 16-(4'-bromobenzal)androsta-1,4-diene-3,17-dione.

5. A compound according to claim 1, which is 16-(4'-N,N-dimethylaminobenzal)androsta-1,4-diene-3,17-dione.

6. A compound according to claim 1, which is 16-(4'-N,N-dimethylamino-2,-fluobenzal)androsta-1,4-diene-3,17-dione.

7. A compound according to claim 1, which is 16-(3',4',5'-trimethoxybenzal)androsta-1,4-diene-3,17-dione.

8. A compound according to claim 1, which is 16-(2',3'-dimethoxybenzal)androsta-1,4-diene-3,17-dione.

9. A compound according to claim 1, which is 16-(4'-ethoxybenzal)androsta-1,4-diene-3,17-dione.

10. A compound according to claim 1, which is 16-(4'-n-propoxybenzal)androsta-1,4-diene-3,17-dione.

11. A compound according to claim 1, which is 16-(4'-n-butoxybenzal)androsta-1,4-diene-3,17-dione.

12. A compound according to claim 1, which is 16-(4'-benzyloxybenzal)androsta-1,4-diene-3,17-dione.

13. A compound according to claim 1, which is 16-(4'-chlorobenzal)androsta-1,4-diene-3,17-dione.

14. A compound according to claim 1, which is 16-(3',4'-methylenedioxybenzal)androsta-1,4-diene-3,17-dione.

15. A compound according to claim 1, which is 16-(4'-acetamidobenzal)androsta-1,4-diene-3,17-dione.

16. A compound according to claim 1, which is 16-(4'-phenylbenzal)androsta-1,4-diene-3,17-dione.

17. A non-linear optical material containing a 16-benzalandrosta-1,4-diene-3,17-dione compound of claim 1.

18. A non-linear optical material according to claim 17, which contains 16-(4,-methoxybenzal)androsta-1,4-diene-3,17-dione.

19. A non-linear optical material according to claim 17, which contains 16-(4,methylthiobenzal)androsta-1,4-diene-3,17-dione.

20. A non-linear optical material according to claim 17, which contains 16-(4,-bromobenzal)androsta-1,4-diene-3,17-dione.

21. A non-linear optical material according to claim 17, which contains 16-(4,-N,N-dimethylaminobenzal)androsta-1,4-diene-3,17-dione.

22. A non-linear optical material according to claim 17, which contains 16-(4'-N,N-dimethylamino-2'-fluorobenzal)androsta-1,4-diene-3,17-dione.

23. A non-linear optical material according to claim 17, which contains 16-(3,-4,-5,-trimethoxybenzal)androsta-1,4-diene-3,17-dione.

24. A non-linear optical material according to claim 17, which contains 16-(2',3'-dimethoxybenzal)-androsta-1,4-diene-3,17-dione.

25. A non-linear optical material according to claim 17, which contains 16-(4'-ethoxybenzal)androsta-1,4-diene-3,17-dione.

26. A non-linear optical material according to claim 17, which contains 16-(4'-n-propoxybenzal)androsta-1,4-diene-3,17-dione.

27. A non-linear optical material according to claim 17, which contains 16-(4'-n-butoxybenzal)androsta-1,4,-diene-3,17-dione.

28. A non-linear optical material according to claim 17, which contains 16-(4'-benzyloxybenzal)androsta-1,4-diene-3,17-dione.

29. A non-linear optical material according to claim 17, which contains 16-(4'-chlorobenzal)androsta-1,4-diene-3,17-dione.

30. A non-linear optical material according to claim 17, which contains 16-(3'-4'-methylenedioxybenzal)androsta-1,4-diene-3,17-dione.

31. A non-linear optical material according to claim 17, which contains 16-(4'-acetamidobenzal)androsta-1,4-diene-3,17-dione.

32. A non-linear optical material according to claim 17, which contains 16-(4'-phenylbenzal)androsta-1,4-diene-3,17-dione.

33. A non-linear optical component using a non-linear optical material containing a 16-benzalandrosta-1,4-diene-3,17-dione compound of claim 1.

34. A non-linear optical component according to claim 33, which uses the non-linear optical material containing 16-(4'-methoxybenzal)androsta-1,4-diene-3,17-dione.

35. A non-linear optical component according to claim 33, which uses the non-linear optical material containing 16-(4'-methylthiobenzal)androsta-1,4-diene-3,17-dione.

36. A non-linear optical component according to claim 33, which uses the non-linear optical material containing 16-(4'-bromobenzal)androsta-1,4-diene-3,17-dione.

37. A non-linear optical component according to claim 33, which uses the non-linear optical material containing 16-(4'-N,N-dimethylaminobenzal)androsta-1,4-diene-3,17-dione.

38. A non-linear optical component according to claim 33, which uses the non-linear optical material containing 16-(4'-N,N-dimethylamino-2'-fluorobenzal)androsta-1,4-diene-3,17-dione.

39. A non-linear optical component according to claim 33, which uses the non-linear optical material containing 16-(3',4',5'-trimethoxybenzal)androsta-1,4-diene-3,17-dione.

40. A non-linear optical component according to claim 33, which uses the non-linear optical material containing 16-(2'-3'-dimethoxybenzal)androsta-1,4-diene-3,17-dione.

41. A non-linear optical component according to claim 33, which uses the non-linear optical material containing 16-(4'-ethoxybenzal)androsta-1,4-diene-3,17-dione.

42. A non-linear optical component according to claim 33, which uses the non-linear optical material containing 16-(4'-n-propoxybenzal)androsta-1,4-diene-3,17-dione.

43. A non-linear optical component according to claim 33, which uses the non-linear optical material containing 16-(4'-n-butoxybenzal)androsta-1,4-diene-3,17-dione.

44. A non-linear optical component according to claim 33, which uses the non-linear optical material containing 16-(4'-benzyloxybenzal)androsta-1,4-diene-3,17-dione.

45. A non-linear optical component according to claim 33, which uses the non-linear optical material containing 16-(4'-chlorobenzal)androsta-1,4-diene-3,17-dione.

46. A non-linear optical component according to claim 33, which uses the non-linear optical material containing 16-(3',4'-methylenedioxybenzal)androsta-1,4-diene-3,17-dione.

47. A non-linear optical component according to claim 33, which uses the non-linear optical material containing 16-(4'-acetamidobenzal)androsta-1,4-diene-3,17-dione.

48. A non-linear optical component according to claim 33, which uses the non-linear optical material containing 16-(4'-phenylbenzal)androsta-1,4-diene-3,17-dione.

49. A process for using a compound of claim 1 as a non-linear optical material in a process for obtaining an emitted light which comprises exposing the non-linear optical material to light.

50. A process for using a compound of claim 1 as a non-linear optical material in a process for obtaining an emitted light which comprises exposing the non-linear optical material in a non-linear optical component to light.

* * * * *